(12) United States Patent
Buela et al.

(10) Patent No.: US 11,578,368 B2
(45) Date of Patent: Feb. 14, 2023

(54) METHODS, TOOLS AND SYSTEMS FOR THE ASSESSMENT, PREVENTION, MANAGEMENT AND TREATMENT SELECTION FOR TYPE 2 DIABETES

(71) Applicant: Patia Biopharma, S.A. De C.V., Benito Juarez, D.F. (MX)

(72) Inventors: Laureano Simón Buela, Benito Juarez, D.F. (MX); Mirella G. Zulueta, Benito Juarez, D.F. (MX)

(73) Assignee: Patia Biopharma, S.A. De C.V., Benito Juarez (MX)

( * ) Notice: Subject to any disclaimer, the term of this patent is extended or adjusted under 35 U.S.C. 154(b) by 276 days.

(21) Appl. No.: 16/860,505

(22) Filed: Apr. 28, 2020

(65) Prior Publication Data

US 2020/0318192 A1   Oct. 8, 2020

Related U.S. Application Data

(63) Continuation of application No. 15/559,236, filed as application No. PCT/EP2016/055949 on Mar. 18, 2016, now abandoned.

(30) Foreign Application Priority Data

Mar. 18, 2015   (GB) ..................... 1504607

(51) Int. Cl.
| | | |
|---|---|---|
| *C12Q 1/68* | (2018.01) | |
| *C12Q 1/6883* | (2018.01) | |
| *C12Q 1/6809* | (2018.01) | |
| *C12Q 1/6858* | (2018.01) | |

(52) U.S. Cl.
CPC ......... *C12Q 1/6883* (2013.01); *C12Q 1/6809* (2013.01); *C12Q 1/6858* (2013.01); *C12Q 2600/118* (2013.01); *C12Q 2600/136* (2013.01); *C12Q 2600/156* (2013.01); *C12Q 2600/158* (2013.01); *C12Q 2600/172* (2013.01)

(58) Field of Classification Search
None
See application file for complete search history.

(56) References Cited

U.S. PATENT DOCUMENTS

2009/0307179 A1   12/2009   Colby et al.

FOREIGN PATENT DOCUMENTS

| JP | 2001-526104 | 12/2001 |
| JP | 2007-267728 | 10/2007 |
| WO | WO 2011/004405 A1 | 1/2011 |

OTHER PUBLICATIONS

Diagram et al. includding supplemental materials (Nature Gen vol. 46, No. 3, Mar. 2014; pp. 234-245 and pp. 1-38 of supplementary information) (Year: 2014).*
Pierce and Ahsan (Human Hered 2010; 69:193-201) (Year: 2010).*
Kahol, "Integrative Gaming: A Framework for Sustainable Game-Based Diabetes Management," *Journal of Diabetes Science and Technology*, vol. 5, No. 2, pp. 293-300, 2011.
Notice of Reasons for Rejection dated Jan. 21, 2020, for corresponding JP Application No. 2017-567545, 14 pages.
Berumen et al., "Influence of Obesity, Parental History of Diabetes, and Genes in Type 2 Diabetes: A Case-Control Study," *Scientific Reports*, 9:2748, 2019 (15 pages).
Diagram et al., "Genome-wide trans-ancestry meta-analysis provides insight into the genetic architecture of type 2 diabetes susceptibility," *Nature Genetics*, vol. 46, No. 3, pp. 234-245, 2014 (including Supplementary Information).
Estrada et al., "Association of a Low-Frequency Variant in HNF1A With Type 2 Diabetes in a Latino Population," *JAMA*, vol. 311, No. 22, pp. 2305-2314, 2014.
Griffin et al., "Diabetes risk score: towards earlier detection of Type 2 diabetes in general practice," *Diabetes Metab Res Rev*, vol. 16, pp. 164-171, 2000.
Herder et al., "The potential of novel biomarkers to improve risk prediction of type 2 diabetes," *Diabetologia*, vol. 57, No. 1, pp. 16-29, 2014.
Lango et al., "Assessing the Combined Impact of 18 Common Genetic Variants of Modest Effect Sizes on Type 2 Diabetes Risk," *Diabetes*, vol. 57, No. 11, pp. 3129-3135, 2008.
LDlink results for linkage between rs4458523 and rs 1801214, all populations; obtained from https://ldlink.nci.nih.gov on May 22, 2019; 1 page, 2019.
LDlink results for linkage between rs4458523 and rs 1801214, MXL+PUR+CLM+PEL; obtained from https://ldlink.nci.nih.gov on May 22, 2019; 1 page, 2019.
Lieberman, "Video Games for Diabetes Self-Management: Examples and Design Strategies," *Journal of Diabetes Science and Technology*, vol. 6, No. 4, pp. 802-806, 2012.
Mahajan et al., "Genome-wide trans-ancestry meta-analysis provides insight into the genetic architecture of type 2 diabetes susceptibility," *Nature Genetics*, vol. 46, No. 3, pp. 234-244, 2014 (Author manuscript version, 27 pages).

(Continued)

*Primary Examiner* — Juliet C Switzer
(74) *Attorney, Agent, or Firm* — Klarquist Sparkman, LLP

(57) ABSTRACT

The present invention provides a method of assessing type 2 diabetes susceptibility and/or predicting treatment responsiveness in a human subject, the method comprising determining the identity of at least one allele at each of three or more positions of single nucleotide polymorphism (SNP) selected from the group consisting of: SLC16A11-rs75493593; HNF1A-rs483353044; TCF7L2-rs7903146; CDKN2A/B-rs10811661; CDKAL1-rs7756992; SLC30A8-rs3802177; IGF2BP2-rs4402960; FTO-rs9936385; PPARG-rs1801282; HHEX/IDE-rs1111875; ADCYS-rs11717195; JAZF1-rs849135; WSF1-rs4458523; INS-IGF2-rs149483638; KCNQ1-rs2237897; and KCNJ11-rs5219, and/or an SNP in linkage disequilibrium with any one of said SNPs at $r^2>0.8$. Also provided are a genotyping tool and a type 2 diabetes risk assessment system for use in the method of the invention.

10 Claims, 8 Drawing Sheets

Specification includes a Sequence Listing.

(56) References Cited

OTHER PUBLICATIONS

Mahajan et al., "Genome-wide trans-ancestry meta-analysis provides insight into the genetic architecture of type 2 diabetes susceptibility," *Nature Genetics*, vol. 46, No. 3, pp. 234-244, 2014.
Mani et al., "The Influence of Social Networks on Patients' Attitudes Toward Type II Diabetes," *J. Community Health*, vol. 36, No. 5, pp. 728-732, 2011.
Martagón et al., "Mexican Carriers of the HNF1A p.E508K Variant do not Experience an Enhanced Response to Sulfonylureas," *Diabetes Care*, vol. 41, No. 8, pp. 1726-1731, 2018.
Mihaescu et al., "Genetic risk profiling for prediction of type 2 diabetes," *PLoS Currents: Evidence on Genomic Tests*, Edition 1, 2011 (22 pages).
Namvaran et al., "Polymorphism of adiponectin (45T/G) and adiponectin receptor-2 (795G/A) in an Iranian population: relation with insulin resistance and response to treatment with pioglitazone in patients with type 2 diabetes mellitus," *Mol. Biol. Rep.*, vol. 39, No. 5, pp. 5511-5518, 2011.
Namvaran et al., "Polymorphism of peroxisome proliferator-activated receptor γ (PPARγ) Pro12Ala in the Iranian population: Relation with insulin resistance and response to treatment with pioglitazone in type 2 diabetes," *European Journal of Pharmacology*, vol. 671, No. 1, pp. 1-6, 2011.
Pierce et al., "Genetic Susceptibility to Type 2 Diabetes is Associated with Reduced Prostate Cancer Risk," *Hum Hered*, vol. 69, pp. 193-201, 2010.
Qi et al., "Genetics of type 2 diabetes in European populations," *Journal of Diabetes*, vol. 4, No. 3, pp. 203-212, 2012 (author manuscript version, 12 pages).
Shetty et al., "Empowering Patients With Diabetes Using Mobile Health Technology," *Empower Magazine*, vol. 5, No. 3, pp. 14-16, 2013.
Sigma Type 2 Diabetes Consortium, "Sequence variants in SLC16A11 are a common risk factor for type 2 diabetes in Mexico," *Nature*, vol. 506, No. 7486, pp. 97-101, 2014.
SNPedia entry for rs4458523. Obtained from https://www.snpedia.com/index.php/Rs4458523 on May 22, 2019. last edited Dec. 5, 2018; 2 pages, 2018.
Syvänen, "Accessing Genetic Variation: Genotyping Single Nucleotide Polymorphisms," *Nature Reviews Genetics*, vol. 2, pp. 930-942, 2001.
Van Leeuwen et al., "A gene variant near ATM is significantly associated with metformin treatment response in type 2 diabetes: a replication and meta-analysis of five cohorts," *Diabetologia*, vol. 55, No. 7, pp. 1971-1977, 2012.
Vassy et al., "Polygenic Type 2 Diabetes Prediction at the Limit of Common Variant Detection," *Diabetes*, vol. 63, No. 6, pp. 2172-2182, 2014 (pre-publication version, 47 pages).
Williams et al., "Sequence variants in SLC16A11 are a common risk factor for type 2 diabetes in Mexico," *Nature*, vol. 506, No. 7486, pp. 97-101, 2014 (including Supplementary Information).
Zulueta et al., "High Performance Two-Step Model for Early Detection and Management of Type 2 Diabetes Risk in the Workplace," *American Diabetes Association, 78th Scientific Sessions*, Jun. 22-26, 2018 (poster, 1 page).
Zulueta et al., "New Diabetes Genetic Risk Assessment Tool for the Prevention of Type 2 Diabetes in Mexico," *ECO2017*, May 17-20, 2017 (poster, 1 page).

\* cited by examiner

Area under the curve

| Result of comparison | Area | standard error (a) | asymptotic (b) | 95% Confidence Interval Lower limit | 95% Confidence Interval Higher limit |
|---|---|---|---|---|---|
| FC1 | 0.666 | 0.023 | 0 | 0.62 | 0.711 |
| FC2 | .652 | .024 | .000 | .605 | .700 |

In the results from comparison, FC1 and FC2, there is at least one match between real positive group and real negative group.

a. According non-parametric assumption b. Null hypothesis: true area = 0.5

FIG. 3B

|  |  |  | FC1 |
|---|---|---|---|
| Risk is lower than population mean | | | 0.5 |
| | | | 0.51-1.0 |
| Risk is higher than population mean | | low | 1.01-1.5 |
| | | medium | 1.51- 2.0 |
| | | high | >2.0 |

FIG. 3C

METHODS, TOOLS AND SYSTEMS FOR THE ASSESSMENT, PREVENTION, MANAGEMENT AND TREATMENT SELECTION FOR TYPE 2 DIABETES

FIELD OF THE INVENTION

The present invention relates to methods and products, in particular arrays and related systems, for in vitro genotyping of type 2 diabetes (T2D) associated genetic variations and to methods for assessment of T2D risk, prevention, management, and treatment selection, including one or more of: assessment of genetic risk for T2D, assessment of sensitivity to diabetes medications, and interventions for supporting diabetes prevention, delay and management, such as mobile individual casual games for reinforcing effective eating habits, virtual longitudinal interactive games, and casual games with real-life behavior assessment, social media networks, and education systems.

BACKGROUND TO THE INVENTION

The global epidemic of Type 2 diabetes (T2D) is a major public health problem, as this disease is the fifth leading cause of death worldwide and a leading cause of morbidity, premature coronary heart disease, stroke, peripheral vascular disease, renal failure, and amputation [1]. The number of individuals living with diabetes worldwide is predicted to increase from 366 million in 2011 to 552 million by 2030 [2].

T2D is a non-insulin-dependent diabetes that is characterized by hyperglycemia due to impaired insulin secretion and insulin resistance in target tissues. T2D is typically diagnosed after age 40 years and is caused by the combined action of genetic susceptibility and environmental factors. T2D is associated with obesity, and it is also a polygenic disease.

Genome-wide association studies (GWAS) for typical T2D forms have identified more than 70 distinct genetic loci carrying common variants that are associated with modest differences in the prevalence of the disease [3, 4, 5]. Because these common variants explain a small fraction of the estimated heritability, it is hypothesized that low-frequency or rare variants of strong effects, not captured by genome-wide association studies but amenable to sequencing approaches, contribute in a meaningful proportion to the genetic architecture of the disease. To date, low-frequency variants with near-complete penetrance have not been found in whole-exome sequencing studies of type 2 diabetes, [6, 7] although a recent whole-genome sequencing study found rare variants associated with type 2 diabetes prevalence in an Icelandic population [8].

As the prevalence of type 2 diabetes in Mexican and Latin American populations is roughly twice that of U.S. non-Hispanic whites, [9, 10] there is an unmet medical need to define the genetic factors that predispose Mexicans and Latin Americans to this disease in order to facilitate intervention and preventive measures. Also needed are methods of treatment selection and treatment regimen optimization specific for Mexican and Latin American populations.

In addition, to prevent onset or complications of diabetes, individuals must manage their diet, exercise, and treatment regimens. Current diabetes management strategies focus on education to drive behavioral change. Diabetes Self-Management Education (DSME) is a technique that involves the diabetic learning the skills needed to manage his/her diabetes and control his/her blood sugar level daily. DSME is a preventive care solution that can help manage diabetes-related complications and reduce overall health costs. Existing diabetes management strategies recognize the need for regular contact, community support, encouragement, and regular monitoring. Most efforts support preventive care with weekly, monthly, or even less frequent contact because frequent contact requires the time of expensive medical professionals. Other methods of controlling diabetes include medication, community health programs, and Internet-based programs to help people manage diabetes.

Nevertheless, there is a serious problem with DSME. As a group, diabetics do not adhere well to regimented programs. Furthermore, methods that have proven to be effective in increasing patient adherence to diabetes management programs do not reach all patients. In fact, existing programs achieve effective self-management (defined as an HbA1C (glycosylated hemoglobin) level of 6.5 mmol/L) in only 10-15% of diabetics. Thus, the majority of diabetics do not adequately adhere to diabetes management programs or fail at self-management. Existing programs do not fully meet the needs of these patients; therefore, additional tools and methods to encourage effective self-management are needed.

SUMMARY OF THE INVENTION

Broadly, the present inventors have found that certain combinations of polymorphisms, particularly single nucleotide polymorphisms (SNPs), are associated with prediction of type 2 diabetes (T2D) risk and treatment response. Further, combinations of SNPs selected for particular suitability to Mexican and Latin American populations, among others, have been identified herein. Further, the SNPs selected for analysis include variations associated to a diversity of ancestral lineage, such diversity being prevalent in the Mexican population. For example, the Mexican population is ethnically diverse, comprising individuals of Mestizo, European descent, Asian Mexican, Afro-Mexican and Indigenous peoples of Mexico. Tools and associated systems have been developed for use in methods of the invention, including for the prediction of T2D susceptibility, treatment selection, management and in some cases prevention of T2D.

Accordingly, in a first aspect the present invention provides a method of assessing type 2 diabetes susceptibility and/or predicting treatment responsiveness in a human subject, the method comprising determining the identity of at least one allele at each of at least 1, 2, 3, 4, 5, 6, 7, 8, 9, 10, 11, 12, 13, 14, 15 or 16 positions of single nucleotide polymorphism (SNP) selected from:

SLC16A11-rs75493593;
HNF1A-rs483353044, (HNF1A E508K);
TCF7L2-rs7903146;
CDKN2A/B-rs10811661;
CDKAL1-rs7756992;
SLC30A8-rs3802177;
IGF2BP2-rs4402960;
FTO-rs9936385;
PPARG-rs1801282;
HHEX/IDE-rs1111875;
ADCY5-rs11717195;
JAZF1-rs849135;
WSF1-rs4458523;
INS-IGF2-rs149483638;
KCNQ1-rs2237897; and
KCNJ11-rs5219,
and/or an SNP in linkage disequilibrium therewith at $r^2>0.8$, $r^2>0.9$, $r^2>0.95$, $r^2>0.99$ or $r^2=1.0$.

The SNPs may be as disclosed in the NCBI dbSNP, Homo sapiens genome build 37.

In some cases in accordance with the first aspect of the invention, the method comprises determining the identity of at least one allele at each of the following SNPs:
SLC16A11-rs75493593;
HNF1A-rs483353044;
KCNQ1-rs2237897; and
TCF7L2-rs7903146.

The four SNPs rs75493593, rs483353044, rs2237897, and rs7903146 represent a compact and efficient SNP set for prediction of T2D susceptibility and sulfonyl therapy response well-adapted to use in an ethnically diverse population, such as a Mexican population. SLC16A11-rs75493593 SLC16A11 has been found to be associated with risk of T2D is Mexican and Latin American individuals. The risk haplotype is present at ~50% frequency in Native American samples and ~10% in east Asian, but is rare in European and African samples. KCNQ1 (including rs2237897) has been implicated as a T2D susceptibility gene in populations of Korean, Chinese and European ancestry as well as in two independent Japanese populations. TCF7L2-rs7903146 has been implicated as a T2D susceptibility gene in populations of European ancestry. As reported herein, preliminary studies indicate that HNF1A-rs483353044 (E508K) is implicated not only as a T2D susceptibility in a Latin American population, but also predicts great hypoglycaemic response to sulfonylurea drugs, such as glipizide among those carrying the E508K variant. Therefore, the combination of the four SNPs rs75493593, rs483353044, rs2237897, and rs7903146 on the SNP genotyping tool of some embodiments of the present invention, advantageously provides useful T2D susceptibility and treatment response information across a wide and ethnically diverse population of subjects.

In some cases in accordance with the first aspect of the invention, the method comprises the method comprises determining the identity of at least one allele at each of the following SNPs:
SLC16A11-rs75493593;
HNF1A-rs483353044;
KCNQ1-rs2237897;
TCF7L2-rs7903146;
FTO-rs9936385; and
PPARG-rs1801282.

In some cases in accordance with the first aspect of the invention, the method comprises the method comprises determining the identity of at least one allele at each of the following SNPs:
SLC16A11-rs75493593;
HNF1A-rs483353044;
TCF7L2-rs7903146;
CDKN2A/B-rs10811661;
CDKAL1-rs7756992;
SLC30A8-rs3802177;
IGF2BP2-rs4402960;
FTO-rs9936385;
PPARG-rs1801282;
HHEX/IDE-rs1111875;
ADCY5-rs11717195;
JAZF1-rs849135;
WSF1-rs4458523;
INS-IGF2-rs149483638;
KCNQ1-rs2237897; and
KCNJ11-rs5219.

In some cases in accordance with the first aspect of the invention, allele determination is carried out at not more than 50, 40, 30, 25, 20, 19, 18, 17 or not more than 16 SNP positions.

In some cases in accordance with the first aspect of the invention presence of one or more of the following risk alleles (i.e. heterozygous or homozygous risk allele) indicates that the subject has greater susceptibility to type 2 diabetes:
T at rs75493593 in SLC16A11;
A at rs483353044 in HNF1A;
T at rs7903146 in TCF7L2;
T at rs10811661 in CDKN2A/B;
G at rs7756992 in CDKAL1;
G at rs3802177 in SLC30A8;
T at rs4402960 IGF2BP2;
C at rs9936385 in FTO;
C at rs1801282 in PPARG;
C at rs1111875 in HHEX/IDE;
T at rs11717195 in ADCY5;
G at rs849135 in JAZF1;
G at rs4458523 in WSF1;
C at rs149483638 in INS-IGF2;
C at rs2237897 in KCNQ1; and
T at rs5219 in KCNJ11.

In some cases in accordance with the first aspect of the invention the method comprises determining the identity of both alleles at each SNP thereby obtaining the genotype of the subject at each SNP.

In some cases in accordance with the first aspect of the invention the subject is determined to be heterozygous or to be homozygous for the risk allele at at least one of said SNPs. In the case where the subject is found to have one or more risk alleles the subject may be classified as being at greater risk of type 2 diabetes in comparison with a subject having none of said risk alleles or having fewer of said risk alleles.

In some cases in accordance with the first aspect of the invention the method comprises assaying a DNA-containing sample that has previously been obtained from said subject. In particular, the sample may be selected from the group consisting of: blood, hair, skin, amniotic fluid, buccal swab, saliva, and faeces. A particularly preferred sample is whole blood, from which has been isolated genomic DNA.

In some cases in accordance with the first aspect of the invention the method comprises isolating and/or amplifying genomic DNA from said subject.

In some cases in accordance with the first aspect of the invention determining the identity of said at least one allele at each SNP comprises: probe hybridization, real time PCR, array analysis, bead analysis, primer extension, restriction analysis and/or DNA sequencing.

In some cases the method employs a plurality of oligonucleotide probes, which plurality includes a pair of allele-specific oligonucleotide probes for each SNP, said allele-specific oligonucleotide probes each spanning the polymorphic position as set forth in the context sequence column of Table 2. Generally such oligonucleotides will be of length 10-50 nucleotides, preferably 12-20 nucleotides, and more preferably 13-18 nucleotides. The skilled person is readily able to design probes that span the SNPs, e.g. making use of the sequence context shown in Table 2. Typically an oligonucleotide probe will comprise of consist of a contiguous sequence of the above-mentioned lengths of the sequence context shown in Table 2 with the polymorphic position typically being located at a central position in each of the allele-specific probes, or its reverse complement or which hybridizes thereto (e.g. under conditions of high stringency).

In some cases determining the identity of said at least one allele at each SNP comprises TaqMan® SNP genotyping. In particular, the method may employ TaqMan® OpenArray® SNP genotyping.

In some cases determining the identity of said at least one allele at each SNP comprises the use of a platform based in an integrated fluidic circuits (IFCs) system, for genotyping. Such platforms are available from, e.g., Fluidigm. In certain cases the platform is a Dynamic Array IFC Genotyping Platform.

In some cases in accordance with the first aspect of the invention the method comprises determining the number of and identity of SNP risk alleles, and wherein the method further comprises computing a type 2 diabetes risk score for said subject.

In some cases the method comprises inputting the SNP risk allele determinations into a probability function to compute said risk score.

In some cases in accordance with the first aspect of the invention said SNPs include the E508K polymorphism in HNF1A, and the presence of at least one A allele at said E508K polymorphism, rs483353044, indicates that the subject will have a greater hypoglycaemic response to antidiabetic therapy with a sulfonylurea as compared with a biguanide. In particular, the sulfonylurea may be Glipizide, Gliclazide, Glibenclamide, Glyburide (Micronase), Glibornuride, Gliquidone, Glisoxepide, Glyclopyramide, Glimepiride (Amaryl), Carbutamide, Acetohexamide, Chlorpropamide or Tolbutamide. Preferably, the sulfonylurea is Glipizide.

In some cases the method is a method of treatment or treatment selection, and further comprises administering, or recommending administration of, sulfonylurea therapy to a type 2 diabetic subject who carries at least one A allele of the E508K polymorphism in HNF1A. In particular, the sulfonylurea may be glipizide.

In some cases in accordance with the first aspect of the invention the subject is of Mexican or Latino American origin or ancestry. In some cases the subject is of European, East Asian, African or Indigenous Mexican origin or ancestry.

In some cases in accordance with the first aspect of the invention the subject has at least one first degree relative who has, or has previously been diagnosed with, type 2 diabetes.

In some cases in accordance with the first aspect of the invention the subject has one or more clinical risk factors for type 2 diabetes selected from: body mass index>30, waist circumference>80 cm for female or >94 cm for male, age>40, impaired glucose regulation, raised fasting blood glucose, and insulin resistance.

In some cases in accordance with the first aspect of the invention the subject is determined to carry one or more of said risk alleles at one or more (e.g. 1, 2, 3, 4, 5, 6, 7, 8, 9, 10, 11, 12, 13, 14, 15 or 16) of said SNPs and therefore to be at greater risk of type 2 diabetes, the method further comprising an intervention selected from the group consisting of:

making a video game electronically accessible to the subject, said video game having predefined game objectives selected to reinforce healthy eating habits that avoid or minimize consumption of diabetogenic food and drink and/or to reinforce exercise habits;

making a movement activity monitor available to the subject, said movement activity monitor being capable of recording and/or reporting movement activity data on the subject to a display interface that presents the movement activity data or a summary or score derived from said data;

making a calorific counter device available to the subject, said device being capable of recording and/or reporting dietary nutritional data on the food and/or drink consumed by the subject; and making a social network available to the subject, said network having type 2 diabetes self-management advice, a plurality of diabetic network participants and a reward system that encourages healthy eating and/or exercise.

In some cases the video game comprises a player character presented with food and/or drink choices, wherein the game rewards selection of healthy food and/or drink by the player character.

In some cases the movement activity monitor comprises a pedometer that communicates or can be configured to communicate to a computer or mobile electronic device (e.g. a mobile telephone such as a smart phone).

In some cases the calorific counter device comprises a mobile electronic device (e.g. a mobile telephone running an application for tracking calorie intake) programmed to receive information on dietary intake of the subject and to display calorific values corresponding the dietary intake.

In some embodiments, the subject is classified into one of the following three risk categories according to the fold-change (FC) value:

low risk: FC between 0 and 1.00
    moderate risk: FC between 1.01 and 1.5;
    intermediate risk: FC between 1.51 and 2.0; and
    high risk: FC greater than 2.0.

In particular, the fold-change value for the subject may be calculated by assigning a risk score for each SNP, wherein the fold-change value is given by multiplying the risk scores of each of the SNPs together. Thus, for example, presence of a risk allele may be assigned a risk score of greater than 1, while presence of a non-risk allele may be assigned a risk score of 1. In particular, for each SNP the risk score may be assigned as follows:

the absence of risk marker, i.e. homozygous non-risk allele genotype, at the SNP is assigned a value of 1,
    the presence of a single risk marker, i.e. heterozygous genotype, at the SNP is assigned a value equal to the odds ratio (OR) for the risk allele at that SNP,
    the presence of two risk markers, i.e. homozygous risk allele genotype is assigned a value equal to the square of the odds ratio $(OR)^2$.

In some cases, the fold-change value is derived by multiplying the risk scores for each SNP together and then dividing by the mean odds ratio (OR) for a control group, i.e. a group of patients previously determined not to have T2D.

In some cases, the OR for the risk allele at each SNP is as follows:

T at rs75493593 in SLC16A11=1.29±0.05;
    A at rs483353044 in HNF1A=5.48±0.05;
    T at rs7903146 in TCF7L2=1.37±0.05;
    T at rs10811661 in CDKN2A/B=1.08±0.05;
    G at rs7756992 in CDKAL1=1.05±0.05;
    G at rs3802177 in SLC30A8=1.12±0.05;
    T at rs4402960 IGF2BP2=1.12±0.05;
    C at rs9936385 in FTO=1.17±0.05;
    C at rs1801282 in PPARG=1.1±0.05;
    C at rs1111875 in HHEX/IDE=1.06±0.05;

T at rs11717195 in ADCY5=1.14±0.05;
G at rs849135 in JAZF1=1.16±0.05;
G at rs4458523 in WSF1=1.13±0.05;
C at rs149483638 in INS-IGF2=1.28±0.05;
C at rs2237897 in KCNQ1=1.31±0.05; and
T at rs5219 in KCNJ11=1.08±0.05.

In particular, the OR may be as set forth in Table 3.

In a second aspect the present invention provides a genotyping tool for use in a method of the first aspect of the invention, said tool comprising an array having a plurality of oligonucleotide probe pairs, each of said probe pairs comprising a first probe specific for a first allele of a single nucleotide polymorphism (SNP) and a second probe specific for a second allele of the SNP, wherein said plurality of oligonucleotide probe pairs comprises probe pairs that interrogate at least three SNPs selected from the group consisting of:
SLC16A11-rs75493593;
HNF1A-rs483353044;
TCF7L2-rs7903146;
CDKN2A/B-rs10811661;
CDKAL1-rs7756992;
SLC30A8-rs3802177;
IGF2BP2-rs4402960;
FTO-rs9936385;
PPARG-rs1801282;
HHEX/IDE-rs1111875;
ADCY5-rs11717195;
JAZF1-rs849135;
WSF1-rs4458523;
INS-IGF2-rs149483638;
KCNQ1-rs2237897; and
KCNJ11-rs5219,
and/or an SNP in linkage disequilibrium with any one of said SNPs at $r^2>0.8$, $r^2>0.9$, $r^2>0.95$, $r^2>0.99$ or $r^2=1.0$.

In some cases the oligonucleotide probes of the array that interrogate SNPs selected from: rs75493593; rs483353044; rs7903146; rs10811661; rs7756992; rs3802177; rs4402960; rs9936385; rs1801282; rs1111875; rs11717195; rs849135; rs4458523; rs149483638; rs2237897; and rs5219, make up at least 50%, at least 60%, at least 70%, at least 80%, at least 90%, at least 95%, at least 99% of the total number of nucleic acid probes in the array, or essentially all of the nucleic acid probes in the array. In this way the genotyping tool is enriched for probes that interrogate SNPs informative for type 2 diabetes risk prediction in Mexican and Latino American populations. By avoiding a high proportion of probes that interrogate other SNPs (e.g. as is typically seen in large-scale SNP microarrays), the genotyping tool of the present invention may provide a more efficient tool for assessment of type 2 diabetes risk prediction whereby use of unnecessary probes and other reagents is minimized.

In some cases said plurality of oligonucleotide probe pairs comprises probe pairs that interrogate at least:
SLC16A11-rs75493593;
HNF1A-rs483353044;
KCNQ1-rs2237897; and
TCF7L2-rs7903146.

In some cases said plurality of oligonucleotide probe pairs comprises probe pairs that interrogate at least:
SLC16A11-rs75493593;
HNF1A-rs483353044;
KCNQ1-rs2237897;
TCF7L2-rs7903146;
FTO-rs9936385; and
PPARG-rs1801282.

In some cases said plurality of oligonucleotide probe pairs comprises probe pairs that interrogate at least:
SLC16A11-rs75493593;
HNF1A-rs483353044;
TCF7L2-rs7903146;
CDKN2A/B-rs10811661;
CDKAL1-rs7756992;
SLC30A8-rs3802177;
IGF2BP2-rs4402960;
FTO-rs9936385;
PPARG-rs1801282;
HHEX/IDE-rs1111875;
ADCY5-rs11717195;
JAZF1-rs849135;
WSF1-rs4458523;
INS-IGF2-rs149483638;
KCNQ1-rs2237897; and
KCNJ11-rs5219.

In some cases the total number of different SNPs for which allele-specific probes are provided does not exceed 50, 40, 30, 25, 20, 19, 18, 17 or 16.

In some cases the allele-specific oligonucleotide probes are each covalently attached to a fluorophore, to a quencher and/or to a minor groove binding domain (MGB). Preferably, each member of an allele-specific probe pair is conjugated to a different fluorophore enabling specific detection of the probe pair members by fluorescence wavelength.

In some cases the nucleotide sequence of each of the allele-specific probes is:
(i) a contiguous nucleotide sequence of 10-25, preferably 13-18 nucleotides, of the sequence context set forth for each SNP in Table 2, wherein the probe sequence spans the polymorphic position; or
(ii) the complement of (i).

In some cases the array further comprises a primer pair for each said SNPs, said primer pair for each SNP comprising an oligonucleotide primer that hybridizes to a target sequence upstream of the SNP and an oligonucleotide primer that hybridizes to a target sequence downstream of the SNP.

In some cases the tool further comprises one or more reagents for amplification of DNA comprising said SNPs and/or for detection of said allele-specific probes. In particular, the tool reagents may include Taq DNA polymerase.

In some cases the array comprises an OpenArray® of between 1000 and 10000 array positions. For example, the array may comprise 3072 through-holes, each acting as a nanoliter-scale reactor (e.g. 33 nL).

Preferably, the tool is in the form of a TaqMan® OpenArray® SNP genotyping platform or an integrated fluidic circuits (IFC) genotyping platform.

In a third aspect, the present invention provides type 2 diabetes risk assessment system for use in a method of the first aspect of the invention, the system comprising a genotyping tool of the second aspect of the invention and a computer programmed to compute a type 2 diabetes risk score from the genotype data of the subject at each of at least three SNPs selected from the SNPs set forth in Table 1 and/or Table 2.

In some cases the computer computes the risk score from the genotype data by applying a weighting or coefficient to each SNP risk allele found to be present such that the contribution of to the risk score is proportional to that SNP's contribution to type 2 diabetes risk, e.g. a weighting commensurate with an odds ratio for the association of the SNP to type 2 diabetes, as set forth in Table 1.

In accordance with the first aspect of the present invention the method of the invention may employ a genotyping tool of the second aspect of the invention or a type 2 risk assessment system of the third aspect of the invention.

The present invention includes the combination of the aspects and preferred features described except where such a combination is clearly impermissible or is stated to be expressly avoided. These and further aspects and embodiments of the invention are described in further detail below and with reference to the accompanying examples and figures.

BRIEF DESCRIPTION OF THE DRAWINGS

FIG. 1A) SLC16A11, INS-IGF2, KCNJ11, HHEX/IDE; FIG. 1B) HNF1A, WFS1, TCF7L2, KCNQ1; FIG. 1C) FTC, CDKN2A/B, ADCY5, CDKAL1; and FIG. 1D) PPARG, IGFBP2, SLC30A8, JAZF1.

FIG. 3B shows Area under the curve (AUC) is determined for FC1 and FC2. FIG. 3C shows the FC1 risk classifications are shown 0.5, 0.51-1.0 (lower than population mean), 1.01-1.5 low risk, 1.51-2.0 medium risk and >2.0 high risk.

DETAILED DESCRIPTION

Single Nucleotide Polymorphisms (SNPs)

Figure 1A:
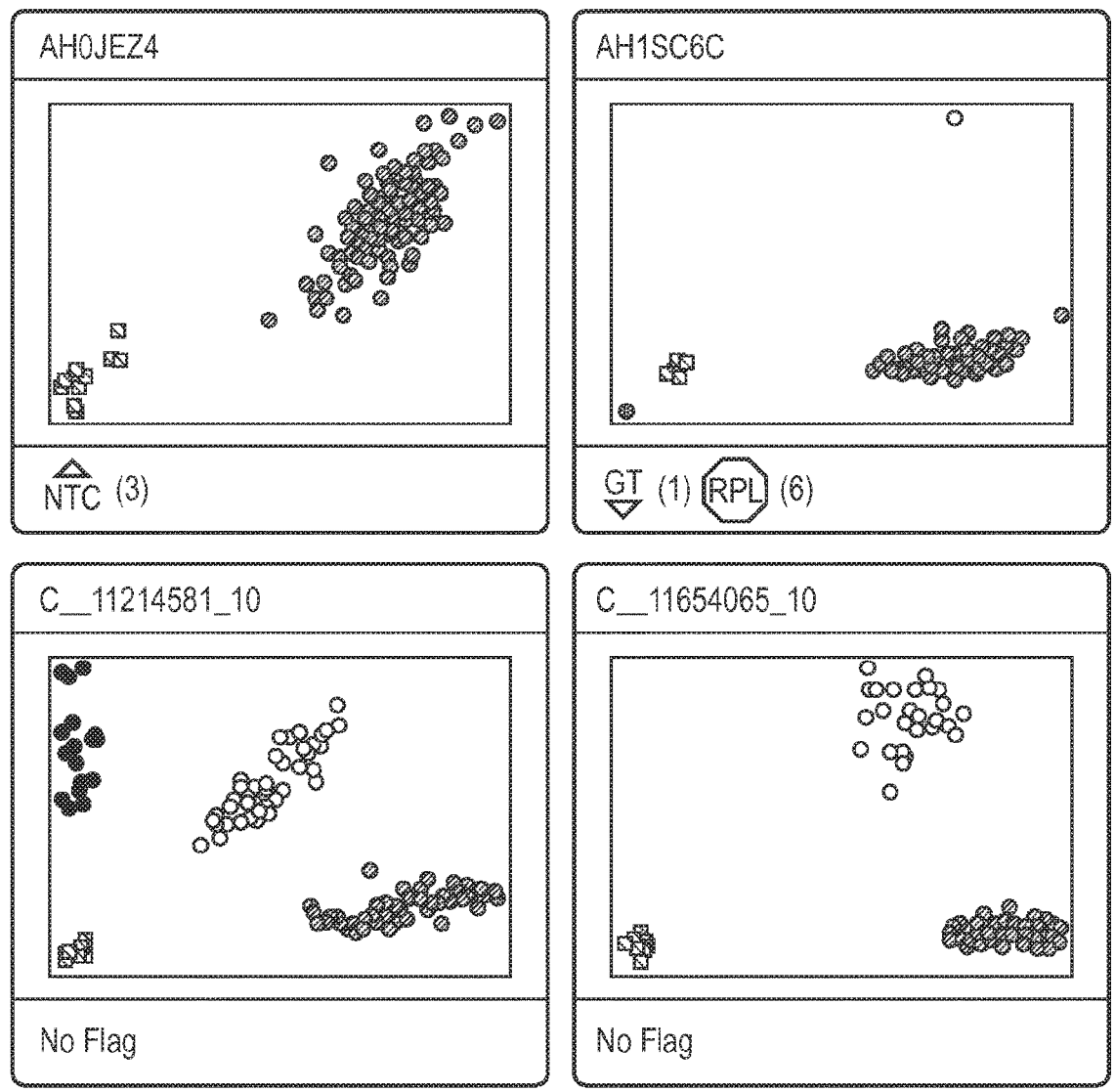
FIGS. 1A-1D shows allelic discrimination plots for each of 16 SNPs employed in the DIABETESpredict SNP genotyping array. The SNPs genotyped are (clockwise from top-left)

SNPs are identified herein using the rs identifier numbers in accordance with the NCBI dbSNP database, which is publically available at: http://www.ncbi.nlm.nih.gov/projects/SNP/. As used herein, rs numbers refer to the dbSNP Homo sapiens build 37.1 available from 2 Feb. 2010.

Linkage Disequilibrium (LD)

In some embodiments, SNPs in linkage disequilibrium with the SNPs associated with the invention are useful for obtaining similar results. As used herein, linkage disequilibrium refers to the non-random association of SNPs at two or more loci. Techniques for the measurement of linkage disequilibrium are known in the art. As two SNPs are in linkage disequilibrium if they are inherited together, the information they provide is correlated to a certain extent. SNPs in linkage disequilibrium with the SNPs included in the models can be obtained from databases such as HapMap or other related databases, from experimental setups run in laboratories or from computer-aided in-silico experiments. Determining the genotype of a subject at a position of SNP as specified herein, e.g. as specified by NCBI dbSNP rs identifier, may comprise directly genotyping, e.g. by determining the identity of the nucleotide of each allele at the locus of SNP, and/or indirectly genotyping, e.g. by determining the identity of each allele at one or more loci that are in linkage disequilibrium with the SNP in question and which allow one to infer the identity of each allele at the locus of SNP in question with a substantial degree of confidence. In some cases, indirect genotyping may comprise determining the identity of each allele at one or more loci that are in sufficiently high linkage disequilibrium with the SNP in question so as to allow one to infer the identity of each allele at the locus of SNP in question with a probability of at least 90%, at least 95% or at least 99% certainty.

As will be appreciated by the reader, in some cases one or more polymorphisms or alterations in linkage disequilibrium with a polymorphism or alteration disclosed herein may find use the methods of the present invention. Linkage disequilibrium (LD) is a phenomenon in genetics whereby two or more mutations or polymorphisms are in such close genetic proximity that they are co-inherited. This means that in genotyping, detection of one polymorphism as present infers the presence of the other. Thus, a polymorphism or alteration in such linkage disequilibrium acts as a surrogate marker for a polymorphism or alteration as disclosed herein. Preferably, reference herein to a polymorphism or alteration in linkage disequilibrium with another means that $r^2>0.8$, preferably $r^2>0.9$, more preferably $r^2>0.95$ or even $r^2>0.99$. In particularly preferred embodiments, an SNP is considered to be in LD with an SNP set forth in Table 1 if it exhibits $r^2=1.0$ and $D'=1.0$.

As used herein, LD is preferably determined in a Mexican or Latino American population.

In one example, the HNF1A E508K SNP (rs483353044) is believed to be in strong LD with the SNP rs143592417 (which encodes Q511R), such that rs143592417 may in some cases be used, in accordance with any aspect of the present invention, as a proxy SNP for rs483353044.

Genotyping Assays

Aspects of the invention relate to determining the presence of SNPs through obtaining a patient DNA sample and evaluating the patient sample for the presence of two or more SNPs. It should be appreciated that a patient DNA sample can be extracted, and a SNP can be detected in the sample, through any means known to one of ordinary skill in art. Some non-limiting examples of known techniques include detection via restriction fragment length polymorphism (RFLP) analysis, planar microarrays, bead arrays, sequencing, single strand conformation polymorphism analysis (SSCP), chemical cleavage of mismatch (CCM), and denaturing high performance liquid chromatography (DHPLC).

In some embodiments, a SNP is detected through PCR amplification and sequencing of the DNA region comprising the SNP. In some embodiments SNPs are detected using microarrays. Microarrays for detection of genetic polymorphisms, changes or mutations (in general, genetic variations) such as a SNP in a DNA sequence, comprise a solid surface, typically glass, on which a high number of genetic sequences are deposited (the probes), complementary to the genetic variations to be studied. Using standard robotic printers to apply probes to the array a high density of individual probe features can be obtained, for example probe densities of 600 features per $cm^2$ or more can be typically achieved. The positioning of probes on an array is precisely controlled by the printing device (robot, inkjet printer, photolithographic mask etc) and probes are aligned in a grid. The organisation of probes on the array facilitates the subsequent identification of specific probe-target interactions. Additionally it is common, but not necessary, to divide the array features into smaller sectors, also grid-shaped, that are subsequently referred to as sub-arrays. Sub-arrays typically comprise 32 individual probe features although lower (e.g. 16) or higher (e.g. 64 or more) features can comprise each subarray.

In some embodiments, detection of genetic variation such as the presence of a SNP involves hybridization to sequences which specifically recognize the normal and the risk allele in a fragment of DNA derived from a test sample. Typically, the fragment has been amplified, e.g. by using the polymerase chain reaction (PCR), and labelled e.g. with a fluorescent molecule. A laser can be used to detect bound labelled fragments on the chip and thus an individual who is homozygous for the normal allele can be specifically distinguished from heterozygous individuals (in the case of autosomal dominant conditions then these individuals are referred to as carriers) or those who are homozygous for the risk allele. In some embodiments, the amplification reaction and/or extension reaction is carried out on the microarray or bead itself.

In some embodiments, methods described herein may involve hybridization. For differential hybridization based methods there are a number of methods for analysing hybridization data for genotyping:

Increase in hybridization level: The hybridization levels of probes complementary to the normal and mutant alleles are compared.

Decrease in hybridization level: Differences in the sequence between a control sample and a test sample can be identified by a decrease in the hybridization level of the totally complementary oligonucleotides with a reference sequence. A loss approximating 100% is produced in mutant homozygous individuals while there is only an approximately 50% loss in heterozygotes. In Microarrays for examining all the bases of a sequence of "n" nucleotides ("oligonucleotide") of length in both strands, a minimum of "2n" oligonucleotides that overlap with the previous oligonucleotide in all the sequence except in the nucleotide are necessary. Typically the size of the oligonucleotides is about 25 nucleotides. However it should be appreciated that the oligonucleotide can be any length that is appropriate as would be understood by one of ordinary skill in the art. In particular, the use of a minor groove binding domain (MBD) permits shorter probe sequences while retaining high discrimination between the perfect match and the mismatch. The increased number of oligonucleotides used to reconstruct the sequence reduces errors derived from fluctuation of the hybridization level. However, the exact change in sequence cannot be identified with this method; in some embodiments this method is combined with sequencing to identify the mutation.

Where amplification or extension is carried out on the microarray or bead itself, three methods are presented by way of example:

In the Minisequencing strategy, a mutation specific primer is fixed on the slide and after an extension reaction with fluorescent dideoxynucleotides, the image of the Microarray is captured with a scanner.

In the Primer extension strategy, two oligonucleotides are designed for detection of the wild type and mutant sequences respectively. The extension reaction is subsequently carried out with one fluorescently labelled nucleotide and the remaining nucleotides unlabelled. In either case the starting material can be either an RNA sample or a DNA product amplified by PCR.

In the Tag arrays strategy, an extension reaction is carried out in solution with specific primers, which carry a determined 5' sequence or "tag". The use of Microarrays with oligonucleotides complementary to these sequences or "tags" allows the capture of the resultant products of the extension. Examples of this include the high density Microarray "Flex-flex" (Affymetrix).

For cost-effective genetic diagnosis, in some embodiments, the need for amplification and purification reactions presents disadvantages for the on-chip or on-bead extension/amplification methods compared to the differential hybridization based methods. However the techniques may still be used to detect and diagnose conditions according to the invention.

Typically, Microarray or bead analysis is carried out using differential hybridization techniques. However, differential hybridization does not produce as high specificity or sensitivity as methods associated with amplification on glass slides. For this reason the development of mathematical algorithms, which increase specificity and sensitivity of the hybridization methodology, are needed (Cutler D J, Zwick M E, Carrasquillo M N, Yohn C T, Tobi K P, Kashuk C, Mathews D J, Shah N, Eichler E E, Warrington J A, Chakravarti A. Genome Research; 11:1913-1925 (2001). Methods of genotyping using microarrays and beads are known in the art.

The genotyping platform for use in the methods of the present invention may be based on the TaqMan® OpenArray® SNP Genotyping system available from Life Technologies. Further details of the TaqMan® genotyping system and OpenArray® format are available from the Life Technologies, Applied Biosystems, webpage, e.g., the TaqMan® OpenArray® Genotyping Getting Started Guide, ©2010 Life Technologies Corporation.

Alternatively or additionally, the genotyping platform for use in the methods of the present invention may be based on the Dynamic Array IFCs Genotyping System from Fluidigm. Further details of the Dynamic Array IFCs Genotyping System are available from Fluidigm webpage.

EXAMPLES

Example 1

Selection of 16 Single Nucleotide Polymorphisms (SNPs) for a Type 2 Diabetes Genetic Prediction Tool in Mexican (and Latino) Populations SNPs were prioritized from the largest meta-analyses of extant genome-wide association studies (GWAS) performed in European and other populations, under the assumptions that: (1) their effects in other populations were generalizable and (2) the largest sample sizes available provided the most robust estimates of the true effect size. The SIGMA1 GWAS dataset was used to ensure that the proposed SNPs have consistent effects in the Mexican population. Consideration was made of allele frequencies in Mexicans, to maximize the predictive power of a SNP at the population level (effect size x allele frequency). To maximize flexibility and minimize cost, a single array of 16 SNPs was chosen. It was decided that the array would not include ancestry informative markers.

SNPs were ranked by their odds ratio in the largest dataset available (Morris et al., Large-scale association analysis provides insights into the genetic architecture and pathophysiology of type 2 diabetes. Nature Genetics (2012) 44:981-990), followed by their P value for association in that GWAS dataset. They were aligned to the same SNPs or to proxies at the same loci in the other two GWAS datasets. Concordance was sought with the transethnic data set from the DIAGRAM Consortium (DIAGRAM Consortium. Genome-wide trans-ancestry meta-analysis provides insight into the genetic architecture of type 2 diabetes susceptibility. Nature Genetics (2014) 46:234-244).

A low frequency variant in HNF1A (c.1522G>A [p.E508K]) has been reported to be associated with type 2 diabetes in a Latino population (The SIGMA Type 2 Diabetes Consortium, JAMA, 2014; 311(22), pp. 2305-2314—the entire contents of which are expressly incorporated herein by reference).

SNPs were rejected if they had allele frequencies <8% in Mexicans (with the exception of HNF1A E508K), or a divergent direction of effect in the SIGMA GWAS (The SIGMA Consortium: Sequence variants in SLC16A11 are a common risk factor for type 2 diabetes in Mexico. Nature (2014) 506:97-101—the entire contents of which are expressly incorporated herein by reference); conversely, they were promoted if they had a P<0.003 (liability model without BMI adjustment) with a constant odds ratio in SIGMA (The SIGMA Consortium, Nature (2014) 506:97-101).

This list was modified based on the following additional criteria: (1) where the SNP assayed in prior publications was in strong linkage disequilibrium with another SNP, for which it served as a near-perfect proxy, the SNP that coded for an amino acid change or which had slightly stronger effects in Mexicans was selected instead (e.g., SLC30A8, KCNJ11, JAZF1).

A variant recently discovered by SIGMA, located in a putative splice site for a highly relevant candidate gene (INS-IGF2), which has a substantial effect in Mexican populations, was also included.

At KCNQ1, the SNP associated with T2D in East Asians and Mexicans was chosen instead of the European SNP because the European SNP was not a good proxy for the East Asian/Mexican SNP.

A consensus list of SNPs was generated (Table 1). Blue font denotes odds ratios and P values obtained for a proxy of the same SNP/locus in SIGMA. Position is indicated according to Build 36 unless otherwise specified.

Table 2 shows target genes, SNP rs identifiers, chromosome and nucleotide location (build 37) and SNP context sequence for each of the 16 SNPs.

TABLE 1

16 SNPs of DIABETESpredict Tool

| Locus | Lead SNP | Chr | Position | Risk | Alt | RAF Eur | RAF Mex |
|---|---|---|---|---|---|---|---|
| SLC16A11 | rs75493593 | 17 | 6,945,087 (build 37) | T | G | 0.02 | 0.30 |
| HNF1A | E508K | 12 | 121,437,091 (build 37) | A | G | N/A | <0.01 |
| TCF7L2 | rs7903146 | 10 | 114,748,339 | T | C | 0.30 | 0.23 |
| CDKN2A/B | rs10811661 | 9 | 22,124,094 | T | C | 0.82 | 0.89 |
| CDKAL1 | rs7756992 | 6 | 20,787,688 | G | A | 0.26 | 0.34 |
| SLC30A8 | rs3802177 | 8 | 118,254,206 | G | A | 0.70 | 0.75 |
| IGF2BP2 | rs4402960 | 3 | 186,994,381 | T | G | 0.31 | 0.25 |
| FTO | rs9936385 | 16 | 52,376,670 | C | T | 0.39 | 0.27 |
| PPARG | rs1801282 | 3 | 12,368,125 | C | G | 0.88 | 0.91 |
| HHEX/IDE | rs1111875 | 10 | 94,452,862 | C | T | 0.58 | 0.64 |
| ADCY5 | rs11717195 | 3 | 124,565,088 | T | C | 0.78 | 0.73 |
| JAZF1 | rs849135 | 7 | 28,162,938 | G | A | 0.52 | 0.67 |
| WFS1 | rs4458523 | 4 | 6,340,887 | G | T | 0.59 | 0.76 |
| INS-IGF2 | rs149483638 | 11 | 2,161,530 (build 37) | C | T | N/A | 0.92 |
| KCNQ1 | rs2237897 | 11 | 2,815,122 | C | T | 0.95 | 0.73 |
| KCNJ11 | rs5219 | 11 | 17,365,206 | T | C | 0.39 | 0.39 |

| Locus | OR Eur Metabochip | P Eur Metabochip | OR Eur transethnic | Meta P transethnic | SIGMA OR no BMI | SIGMA P no BMI |
|---|---|---|---|---|---|---|
| SLC16A11 | N/A | N/A | N/A | N/A | 1.29 (1.20-1.38) | $5.5 \times 10^{-12}$ |
| HNF1A | N/A | N/A | N/A | N/A | 5.48 (2.83-10.61) | $4.4 \times 10^{-7}$ |
| TCF7L2 | 1.39 (1.35-1.42) | $1.2 \times 10^{-39}$ | 1.40 (1.35-1.46) | $7.8 \times 10^{-75}$ | 1.37 (1.27-1.48) | $3.6 \times 10^{-15}$ |
| CDKN2A/B | 1.18 (1.15-1.22) | $3.7 \times 10^{-27}$ | 1.18 (1.13-1.24) | $1.1 \times 10^{-27}$ | 1.08 (0.98-1.20) | $1.3 \times 10^{-1}$ |
| CDKAL1 | 1.17 (1.14-1.20) | $7.0 \times 10^{-35}$ | 1.20 (1.16-1.25) | $1.6 \times 10^{-26}$ | 1.05 (0.98-1.13) | $1.7 \times 10^{-1}$ |
| SLC30A8 | 1.14 (1.11-1.17) | $1.3 \times 10^{-21}$ | 1.16 (1.11-1.22) | $1.8 \times 10^{-18}$ | 1.12 (1.05-1.21) | $1.8 \times 10^{-3}$ |
| IGF2BP2 | 1.13 (1.10-1.16) | $2.4 \times 10^{-23}$ | 1.13 (1.09-1.17) | $9.5 \times 10^{-18}$ | 1.12 (1.04-1.20) | $2.3 \times 10^{-3}$ |
| FTO | 1.13 (1.10-1.16) | $2.6 \times 10^{-23}$ | 1.13 (1.09-1.18) | $1.2 \times 10^{-12}$ | 1.17 (1.08-1.27) | $1.1 \times 10^{-4}$ |
| PPARG | 1.13 (1.09-1.17) | $1.1 \times 10^{-12}$ | 1.16 (1.10-1.23) | $5.7 \times 10^{-10}$ | 1.10 (1.00-1.21) | $4.0 \times 10^{-2}$ |
| HHEX/IDE | 1.11 (1.09-1.14) | $2.0 \times 10^{-19}$ | 1.15 (1.11-1.19) | $3.2 \times 10^{-19}$ | 1.06 (0.99-1.13) | $9.0 \times 10^{-2}$ |
| ADCY5 | 1.11 (1.08-1.14) | $6.5 \times 10^{-14}$ | 1.09 (1.05-1.14) | $2.2 \times 10^{-8}$ | 1.14 (1.06-1.22) | $2.7 \times 10^{-4}$ |

TABLE 1-continued

16 SNPs of DIABETESpredict Tool

| | | | | | | |
|---|---|---|---|---|---|---|
| JAZF1 | (1.08-1.13) 1.10 | $3.1 \times 10^{-17}$ | (1.08-1.17) 1.09 | $1.7 \times 10^{-9}$ | (1.08-1.24) 1.13 | $2.3 \times 10^{-5}$ |
| WFS1 | (1.07-1.12) | $2.0 \times 10^{-15}$ | (1.06-1.13) | $2.1 \times 10^{-9}$ | (1.05-1.21) 1.28 | $1.2 \times 10^{-3}$ |
| INS-IGF2 | N/A | N/A | N/A | N/A | (1.08-1.51) | $3.5 \times 10^{-3}$ |
| KCNQ1 | 1.09 | $1.2 \times 10^{-11}$ | 1.09 | $1.7 \times 10^{-14}$ | 1.31 | $8.0 \times 10^{-13}$ |
| KCNJ11 | (1.06-1.11) 1.07 | | (1.04-1.13) 1.08 | | (1.22-1.41) 1.08 | |
| | (1.05-1.10) | $8.5 \times 10^{-10}$ | (1.04-1.12) | $3.2 \times 10^{-11}$ | (1.01-1.15) | $2.3 \times 10^{-2}$ |

TABLE 2

SNP Context Sequence

| Target | rs ID | Location (b. 37) | SNP Context Sequence | SEQ ID NO: |
|---|---|---|---|---|
| TCF7L2 | rs7903146 | ch. 10: 114758349 | TAGAGAGCTAAGCACTTTTTAGATA[C/T]TATATAATTTAATTGCCGTATGAGG | 1 |
| — | rs10811661 | ch. 9: 22134094 | CAGCTCACCTCCAGCTTTAGTTTTC[C/T]CATGACAGTAAGTCTATTACCCTCC | 2 |
| CDKAL1 | rs7756992 | ch. 6: 20679709 | ATATTCCCCCCTGTATTTTAGTTTT[A/G]GATCTACAGTTATGTAGCAATGAGC | 3 |
| SLC30A8 | rs3802177 | ch. 8: 118185025 | TAAGGAACCAAAGGAAGAAATTCAT[A/G]TCATGGTGCAATGCACATTTTATCT | 4 |
| IGF2BP2 | rs4402960 | ch. 3: 185511687 | AGTAAGGTAGGATGGACAGTAGATT[G/T]AAGATACTGATTGTGTTTGCAAACA | 5 |
| FTO | rs9936385 | ch. 16: 53819169 | CATATGAAGAGGGATTTTTTTGCCT[C/T]CTTGGTTCACTGCATATTCCCAGTA | 6 |
| — | rs1111875 | ch. 10: 94462882 | GACCCTGAGTGCAGGTTCAGACGTC[C/T]AGAGGAAATGACTTGATGGTACGGA | 7 |
| ADCY5 | rs11717195 | ch. 3: 123082398 | TTGAACAGGGCTTTATGTCCGAGGA[C/T]GATTATAAAATTTAACAATTAGGAG | 8 |
| JAZF1 | rs849135 | ch. 7: 28196413 | ACCACTGCTCTATAAGCAAGAGTAC[A/G]TCACCAAGAAATTTAAATTCAGATC | 9 |
| KCNQ1 | rs2237897 | ch. 11: 2858546 | TCAGTGGTGCCCAGGGAGCTGGGGA[C/T]GAGGGGCCTCATCCTTCCCCTGAGC | 10 |
| KCNJ11 | rs5219 | ch. 11: 17409572 | CGCTGGCGGGCACGGTACCTGGGCT[C/T]GGCAGGGTCCTCTGCCAGGCGTGTC | 11 |
| HNF1 | rs483353044 | ch. 12: 121437101 | GCCAGCCCTCTACAGCCACAAGCCC[G/A]AGGTGGCCCAGTACACCCACACGGG | 12 |
| WFS1 | rs4458523 | ch. 4: 6289986 | AATTTCTTTCCTGACCTCACAGCCA[G/T]ATTGTACTTTAAAGTTCCTCCCACA | 13 |
| SLC16A11 | rs75493593 | ch. 17: 6945087 | GGAAGCAGCTCCCCCGTCTCTGGGG[G/T]AGGCGTGGCTGGAGGGGAGGCTGGA | 14 |
| INS-IGF2 | rs149483638 | ch. 11: 2161530 | TTTGGGGGTCTGGGGAAACCATCTC[C/T]TGGAGAGTTTGAACGATGTAAGAAA | 15 |
| PPARG | rs1801282 | ch. 3: 12393125 | AACTCTGGGAGATTCTCCTATTGAC[C/G]CAGAAAGCGATTCCTTCACTGATAC | 16 |

The TaqMan® OpenArray® genotyping system (Life Technologies Corp., Carlsbad, Calif.) can be employed as a high-throughput platform for genotyping subject-derived DNA samples at each of the 16 SNPs identified in Table 1.

For each SNP, two allele-specific probes were provided. Each of the allele-specific probes is conjugated to a fluorescent dye, a quencher and a minor groove binding (MGB) domain. The fluorescent reporter dyes are chosen so that the probe specific for the risk allele is distinguishable from the probe specific for the non-risk allele at the SNP in question. For example, the fluorophores VIC and 6-FAM were employed and were covalently attached to the 5' end of the respective allele-specific probe. Near the 3' end of the allele-specific probe, a non-fluorescent quencher was attached. The MGB increases the melting temperature (Tm) of the probes providing great separation between matched and mismatched probes and thereby increasing genotyping accuracy. Also provided are forward and reverse primers that flank the SNP of interest.

Pre-designed primers and allele-specific probes are commercially available for the TaqMan® genotyping system. For example, TaqMan genotyping reagents for rs7903146 in TCF7L2 are available from Life Technologies under the product code C_29347861_10.

Further details of the TaqMan® genotyping system and OpenArray® format are available from the Life Technologies, Applied Biosystems, webpage, e.g., the TaqMan® OpenArray® Genotyping Getting Started Guide, © 2010 Life Technologies Corporation.

The 3072 through-hole OpenArray® format was chosen, each through-hole acting as a 33 nL reactor. This plate format allows examination of 144 samples against the 16 unique SNPs per plate.

Figure 1B:
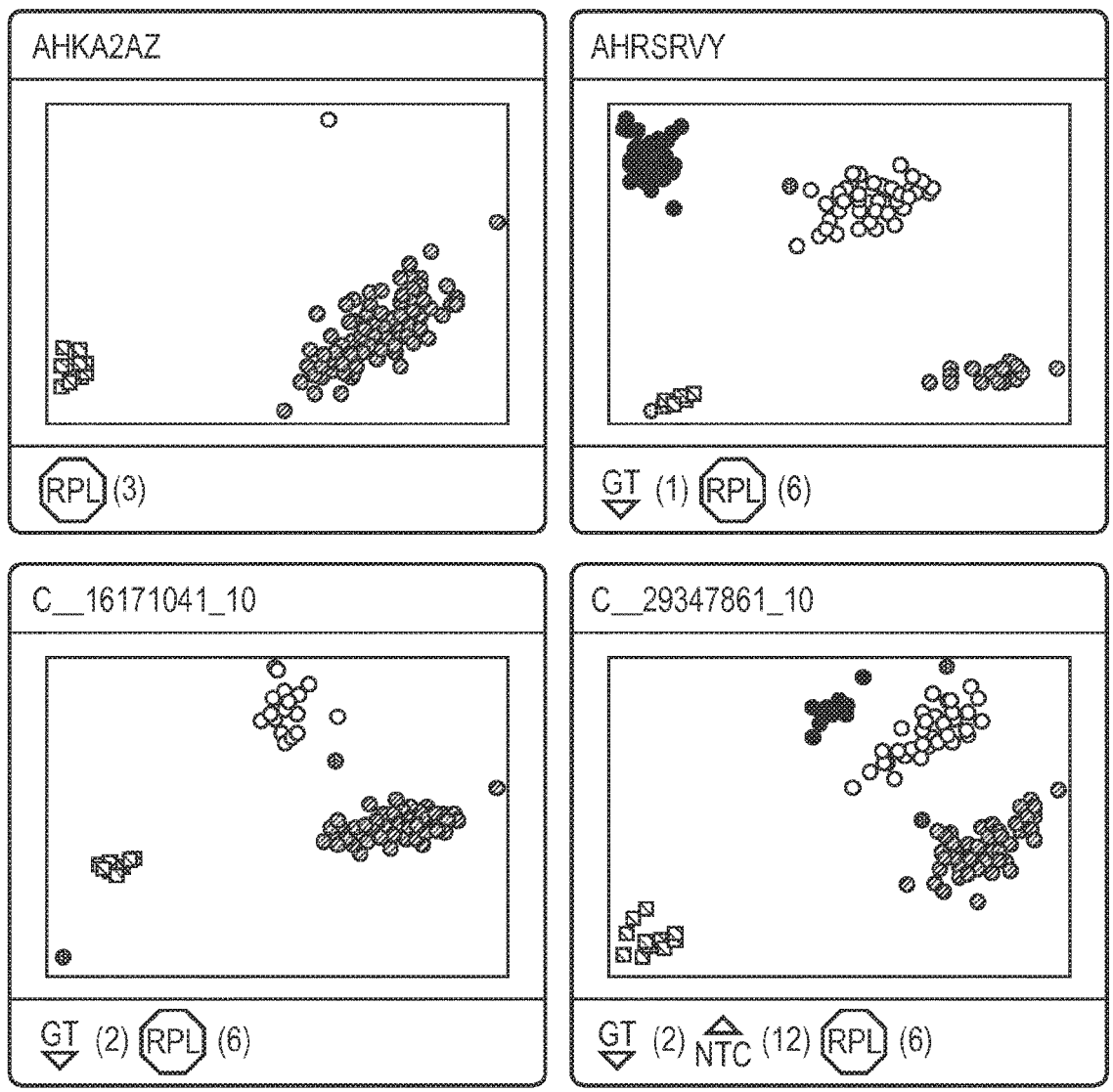
Figure 1C:
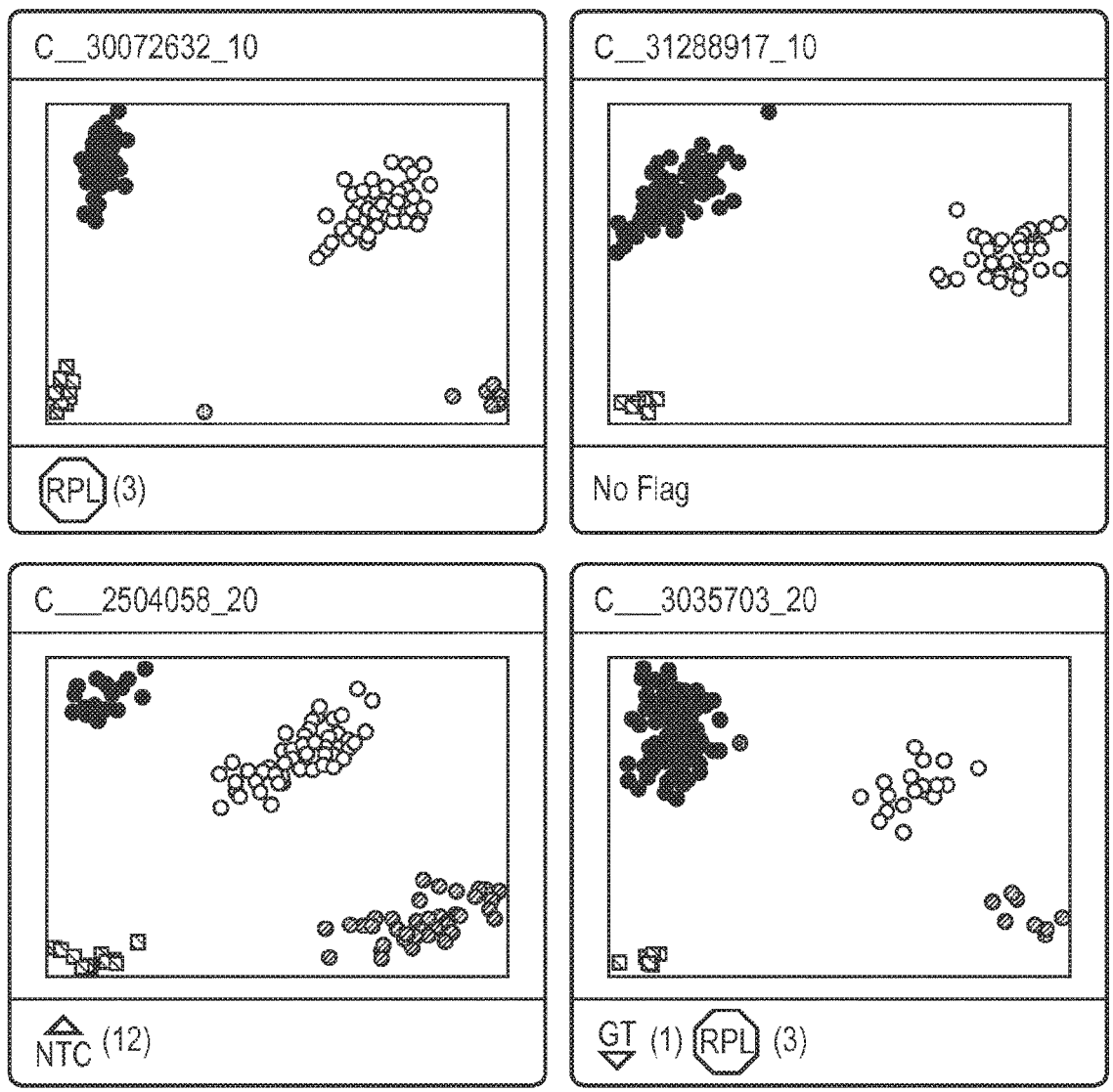
Figure 1D:
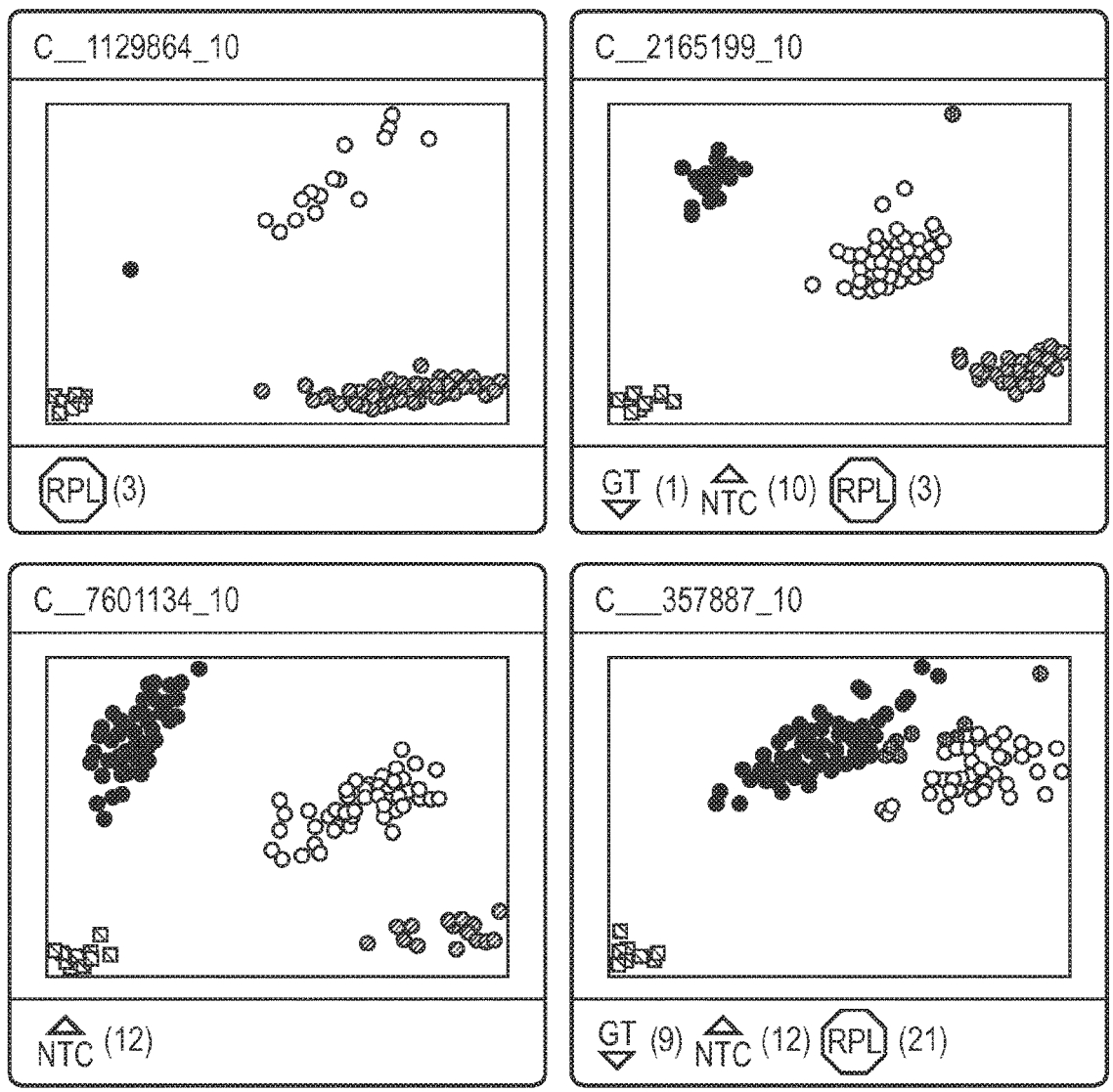
Figure 2:
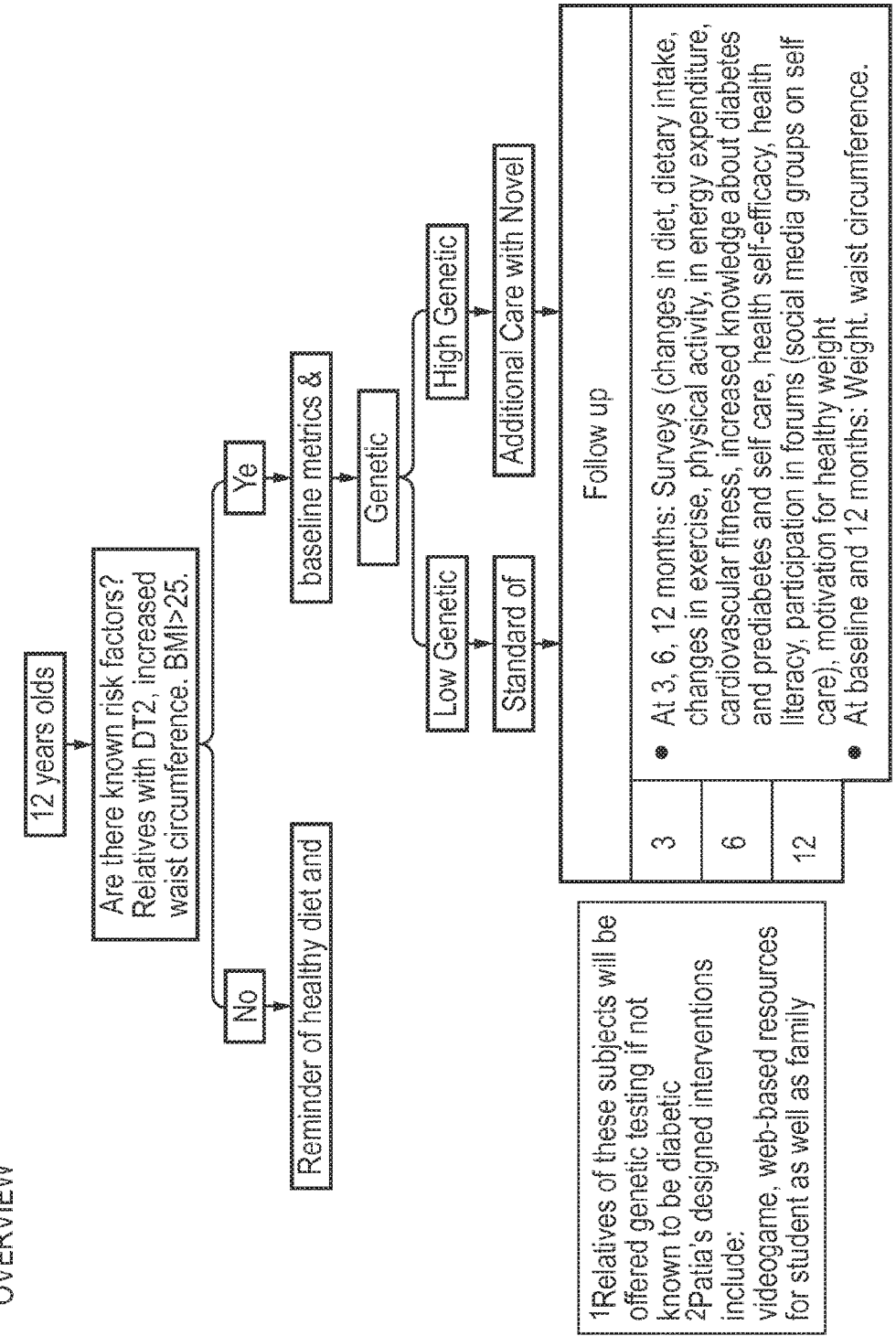
FIG. 2 shows a flow-chart decision tree indicating the application of the the DIABETESpredict tool to determine type 2 diabetes genetic risk and therefore the appropriate level of intervention, including diabetes management self care.
Figure 3A:
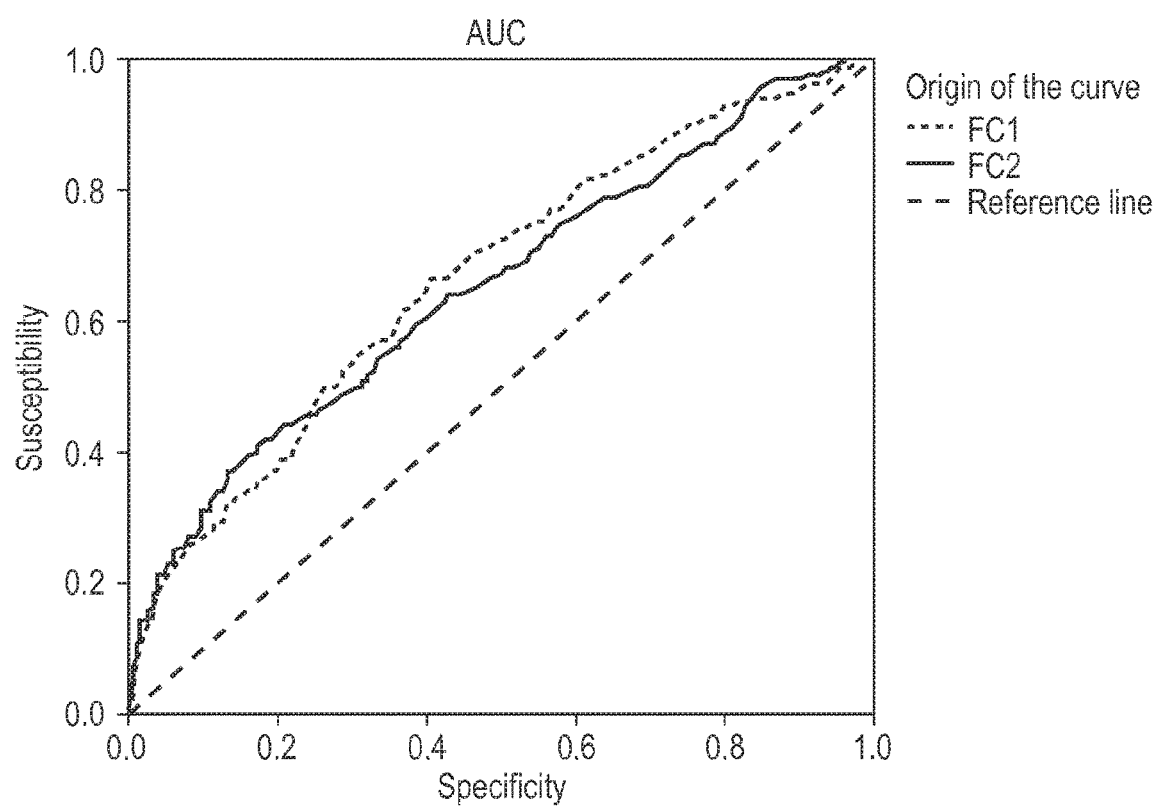
FIG. 3A shows a receiver operating characteristic (ROC) curve in which susceptibility (y-axis) is plotted against 1-specificity (x-axis) for FC1 (blue curve) and FC2 (green curve). A reference line is shown in yellow. The diagonal segments are produced by the draws.
Figure 4:
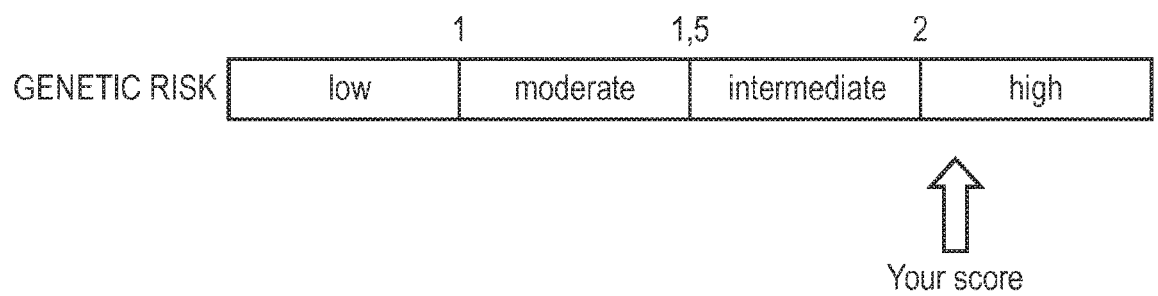
FIG. 4 shows a genetic risk spectrum low (<1), moderate (1-1.5), intermediate (1.5-2) and high (>2). An example score "Your score" is depicted by the arrow head pointing to the high genetic risk region on the right hand side of the genetic risk spectrum.

Genotyping results shown in FIG. 1. Each of homozygous allele 1, heterozygous and homozygous allele 2 is distinguished demonstrating that the TaqMan® OpenArray® SNP Genotyping platform is able to discriminate the different possible genotypes at each of the 16 SNP targets.

Example 2

Study to Determine the Genetics of Acute Glipizide and Metformin Response in Humans with the HNF1A E508K Variant As described in The SIGMA Type 2 Diabetes Consortium, JAMA, 2014; 311(22), pp. 2305-2314, a mutation in HNF1A was identified, which is present in 2% of people with diabetes studied in Mexico. This mutation is located in exon 8 (E508K), which causes a partial defect in the function of the protein. This finding is consistent with that has been observed in other described mutations of exon 8; and is associated with late-onset diabetes. The initial clinical and biochemical characterization of subjects with the HNF1A E508K mutation showed that carriers of the variant have a clinical profiles indistinguishable from those of patients with Type 2 Diabetes. Pharmacogenetic studies are required to demonstrate that the carriers with the E508K variant selectively respond to sulfonylureas. Testing of this hypothesis has practical implications because it would be possible to propose a simple and inexpensive genetic test that helps clinicians select the appropriate pharmacological treatment in a significant number of cases.

Hypothesis

Individuals with the risk allele E508K of HNF1 alpha will have a greater hypoglycemic response to glipizide and a similar response to those of metformin compared to the control subjects matched up by age and gender.

Description of the Ongoing Study

Acute and medium-term response to glipizide in patients with and without the E508K variant of HNF1A will be measured. The study will consist of two phases. Patients will be invited to participate in both, but the research subject will have the freedom to choose only one of the stages of the study.

Stage 1

Open Study of a Single Dose of Glipizide (5 mg) in Patients With and Without the E508K Variant of HNF1A Main Objective: To compare the change in glucose between carriers and noncarriers after a single oral administration of 5 mg of glipizide.

Secondary objectives are: (1) to compare the change of the plasma insulin concentration between carriers and non-carriers after a single oral administration of 5 mg of glipizide and (2) to compare the number of patients suffering from symptomatic hypoglycemia between carriers and non-carriers after a single oral administration of 5 mg of glipizide.

Study Design

This will be a single center, open study. Approximately 100 eligible subjects with type 2 diabetes in Mexico will be included in the study in two groups. In the first group, 50 patients carrying the p.E508K mutation in HNF1A will be included ("carriers"). Patients will be recruited from existing databases in which they have already been genotyped as carriers of HNF1A p.E508K. In the second group, 50 patients will be invited that do not present the mutation in HNF1A p.E508K ("noncarriers"). The inclusion of non-carrier group will begin after the carrier group completes the study procedures, in order to select the controls taking into account case characteristics of sex, BMI, age, and age of diabetes onset. Patients in the group of non-carriers can be identified from the same database or other sources. An additional group of 25 patients with MODY3 loss of function in HNF1A will be recruited from Norway and will serve as a positive control for the experimental condition (an increased sensitivity to sulfonylurea). Patients will be eligible for the study if they have: (1) Type 2 Diabetes; (2) treat themselves with less than two oral antidiabetic agents; (3) can safely undergo a 7-day washout of antidiabetic drugs; (4) have HbA1c ≤7.5%; and (5) do not have an allergy or intolerance to glipizide or other medications with homology to sulfonylureas.

Eligible patients will discontinue antidiabetic therapy and initiate a washout period of 7 days, during which they will be monitored for hyperglycemia requiring re-initiation of antidiabetic therapy. If the fasting blood glucose is ≥250 mg/dl (13.9 mmol/l) during the washout period, the patient should contact the study center within 24 hours, and the investigator will determine whether the participant must try to improve diet and exercise to maintain glycemic control or if the participant has to end their participation in the study and restart treatment. The patient will be excluded from further participation if more than 2 blood glucose values in consecutive fasting are ≥250 mg/dl. Patients who do not receive the drug treatment for hyperglycemia will skip the washout period and will start the study treatment.

Patients will be admitted to the clinical research center after fasting for 8 hours. An intravenous angiocatheter 20 g or 22 g will be inserted for blood draws at multiple time points. Samples will be obtained during fasting periods. Patients with a fasting blood glucose (based on the assessment made using a glucometer) of >80 mg/dl will receive glipizide 5 mg orally. Subjects with blood glucose <80 mg/dl will not receive the dose of glipizide. The concentrations of glucose, insulin and other hormones (GLP1) and metabolites will be measured at 15, 30, 60, 90, 120, 180, and 240 minutes after administration of 5 mg of glipizide. In the event of developing symptoms of hypoglycemia, blood glucose will be measured immediately. The patient will receive hypoglycemia intervention by ingesting carbohydrates if blood glucose is <50 mg/dL with or without symptoms of hypoglycemia, or if blood glucose is <70 with symptoms of hypoglycemia. All patients will be given a meal high in carbohydrates and fat at the end of the study visit. The visit will end when: 1) the patient completes an observation period of 240 minutes or has been intervened due to hypoglycemia and 2) the value of blood glucose 30 minutes after meal completion of the study is >80 mg/dl.

Participants will be instructed to eat more carbohydrates, if blood glucose values <80 mg/dl. After completion of the study protocol, patients will be advised to resume their antidiabetic therapy.

Statistical Methods

The primary objective is to compare the glucose response between carriers and noncarriers after administration of glipizide. The primary endpoint will be the delta of the glucose concentration during the test. Secondary endpoints will be the lesser of glucose (with or without adjustment for baseline glucose) and the area under the glucose curve during curve (adjusted for baseline glucose). Other secondary endpoints include the change in the concentration of insulin and the number of patients suffering from symptomatic hypoglycemia. The insulin peak value (adjusted for basal insulin) to serve as the final evaluator of the effect of insulin secretion. We assume a 18 mg/dl (1 mmol/L) difference in glucose delta between carriers and non-carriers, a standard deviation of 27 mg/dl (1.5 mmol/L), and alpha=0.05. Therefore, we have a power of 85% with 41 subjects in each group. Fifty patients will be enrolled in each group to ensure a sufficient number of evaluable subjects.

Stage 2

An Open Study to Compare the Effect of 12 Week Treatment with Glipizide or Metformin on HbA1c in Carriers of HNF1A Variant Assay p.E508K Main Objective: To compare the decrease in HbA1c levels between carriers and non-carriers of the mutation p.E508K HNF1A after 12 weeks of treatment with glipizide or metformin.

Secondary objectives are to compare the following variables between treatment groups and between carriers and non-carriers: fasting blood glucose, postprandial blood glucose and insulin, fructosamine, number of symptomatic hypoglycemias, adverse effects and cases that did not tolerate the maximum dose given.

Study Design

This is a single center, open study, parallel group, randomized, 12-week study, aimed at comparing the effect of glipizide and metformin among carriers of the p.E508K HNF1A mutation. Approximately 100 patients with this mutation in HNF1A p.E508K will be enrolled ("carriers"). Patients will be recruited from existing databases of persons already genotyped as carriers of p.E508K HNF1A.

Patients will be eligible for the study if they: (1) have Type 2 Diabetes; (2) are treated by less than two oral antidiabetic agents; (3) can safely undergo a wash of 6 weeks of antidiabetic drugs; (3) have HbA1c between 7-10%; (4) have estimated glomerular filtration rate greater than 60 ml/min/1.73 m$^2$ and have AST and ALT <2.5 times higher than normal limit; (5) no allergy or intolerance to glipizide, metformin or other medications with homology to sulfonylureas.

Eligible patients will suspend their antidiabetic therapy and have a washout period of 6 weeks, during which they will be monitored in a timely manner to detect the presence of hyperglycemia requiring re-initiation of antidiabetic therapy. All patients will be given a diet and exercise plan at the beginning of the washout period. Patients will be instructed to measure their capillary fasting plasma glucose. If blood glucose is ≥250 mg/dl (13.9 mmol/l) during the washout period, the patient should contact the study center within 24 hours, and the investigator will determine if the participant should begin treatment with a pharmacological inhibitor of DPP-IV for glucose control. The patient will be excluded from further participation if, after starting therapy with DPP-IV, they have more than 2 blood glucose values at consecutive fasting ≥250 mg/dl during the washout period. Patients with blood glucose 250 mg/dl (13.9 mmol/L) and symptoms of hyperglycemia will resume their prior antidiabetic treatment in accordance with the standard of care. Patients who do not receive drug treatment for hyperglycemia will skip the washout period and will start the study treatment.

At the conclusion of the washout period, 100 patients will be drawn for a period of (1:1) treatment with metformin and glipizide. Participants will be stratified into four groups based on the initial value of HbA1c in the washout period (7.0-9.0% or 9.1-10.5%) and based on treatment status at the beginning of the period of primary treatment (untreated vs treated with DPP-IV). If the patient is taking a DPP-IV at randomization, this medicine may continue throughout the period of primary treatment.

Before receiving the first dose of treatment, all patients will be referred to the research center after 8 hours fasting (treatment day 1). An intravenous angiocatheter 20 g or 22 g will be inserted for blood draws at multiple time points. Samples to be obtained during fasting. Patients will undergo a test to gauge mixed meal tolerance, to be completed 15 minutes after starting the meal. Blood glucose, insulin, and the sample for further investigative measures will be assessed at 15, 30, 60, 90, 120, 180, and 240 minutes after starting the meal. At the end of the observation period of 240 minutes, patients will receive a diet high in carbohydrates and fat. The first dose of study medication will be administered at the research center. Patients will receive glipizide (5 mg, orally) or metformin (500 mg orally). Patients will have an assessment of capillary glucose 1 hour after the high carbohydrates and fat meal; and will be discharged if their blood glucose is above 80 mg/dl.

Patients will then begin the outpatient phase of the study treatment on Day 2. For patients randomized to receive metformin, they will initiate a dose of 500 mg twice daily for 1 week, then 500 mg every morning and 500 mg every night for one week, and then 1 g twice daily for the remaining 10 weeks. Patients will begin taking glipizide at 5 mg twice daily for 1 week, followed by 10 mg twice a day for 1 week, and 20 mg twice daily for the remaining 10 weeks. The treatment dose will be reduced to half if there are more than 2 episodes of symptomatic hypoglycemia or any other side effects related to the study drugs administered. Patients will be asked to measure their fasting capillary blood glucose at least two days a week.

Patients will return to the clinic after 6 weeks and 12 weeks of treatment for a blood sample to be taken under fasting conditions and review of medication compliance and tolerance. Patients with more than 2 values in consecutive blood glucose fasting 250 mg/dl or severe signs and symptoms of hyperglycemia during the main treatment will begin additional antidiabetic therapy. Therapies other than metformin or sulfonylureas during the main treatment for the control of severe hyperglycemia agents will be allowed. After 12 weeks of treatment a test of mixed meal will be performed, similar to the one conducted at the beginning of the treatment. Intravenous angiocatheter 20 g or 22 g will be placed for blood draws at multiple time points, with samples to be obtained during fasting. Patients will undergo a test of mixed meal tolerance, to be completed 15 minutes after starting the meal. They will take the appropriate dose assigned at the beginning of the test treatment. Blood glucose, insulin, and the sample for further investigative measures will be assessed at 15, 30, 60, 90, 120, 180, and 240 minutes after starting the meal. At the end of the observation period of 240 min, patients will receive a diet high in carbohydrates and fat. After completion of the study protocol, patients will resume using the antidiabetic therapy prior to study.

Statistical Methods

The primary objective will be to compare the reduction in HbA1c at 12 weeks of glipizide or metformin. The reduction in HbA1c at week 12 will be compared between baseline glipizide and metformin using analysis of covariance (ANCOVA), adjusted for stratification factors at randomization (state at the start of the treatment period, and HbA1c main treatment). The analysis with respect to the primary endpoint will be conducted focusing on an intention to treat approach and one that includes only those cases who completed the study. The secondary objective is to compare the changes in fasting glucose, changes in post-prandial glucose and insulin, fructosamine change, weight, rates of hypoglycemia, general safety, and the number of patients not achieving dose maximum treatment. These criteria will be exploratory and not adjusted for multiplicity.

For the primary endpoint, a reduction in HbA1c of −0.66% is assumed in the glipizide group vs. metformin group, a standard deviation of 1.1%, and $\alpha$=0.05. Therefore, the power of the study is 80% with 45 subjects in each group. Fifty patients will be enrolled in each group to ensure a sufficient number of evaluable subjects.

Potential Benefits of the Study

If the study obtains positive results, the study will justify studies with long-term monitoring that measure clinical outcomes. The ultimate goal is to integrate the results from these genetic studies into clinical applications.

Justification of Study Drugs

Glipizide was selected because it has a high oral absorption rate, it starts acting within 30 minutes and its life is short (2-8 hours). The proposed dose (5 mg) is usually the starting dose used in patients with Type 2 Diabetes. The risk of inducing severe hypoglycemia is low (0.19-2.5 episodes per 1000 patient-years). Metformin is the only biguanide available. It is the basis of the pharmacological treatment of diabetes. The proposed dose is associated with a low rate of gastrointestinal adverse events. The drugs will be provided to participants at no cost.

Laboratory Procedures

Commercial reagents will be used for the measurement of glucose, insulin, C-peptide, creatinine and GLP1. A pregnancy test will be administered to women who are within their reproductive age using the first morning urine.

Potential risks and discomforts:

No vulnerable populations, pregnant women or patients with conditions considered contraindications to the use of study drugs (such as liver failure and renal failure (<60 ml/min/1.73 m$^2$) will be included.

Expected discomfort is hypoglycemia symptoms caused by venipuncture, gastrointestinal effects (diarrhea and flatulence) caused by metformin and stress to participate in a research study or the knowledge of the existence of abnormalities in carbohydrate metabolism. To reduce the risk of severe hypoglycemia repeated capillary glucose measurements will be taken and the protocol in place reduces exposure of patients to medicines if their blood sugar is considered to be at risk (see previous paragraphs). Resources required to treat hypoglycemia by administering glucose orally or intravenously will be available. The total blood volume at visit 1 is 167 ml and 118 ml at visit 2. The samples will be obtained by trained personnel. The expected discomforts are skin lesions, bruising and pain. Metformin can cause bloating or diarrhea. If diarrhea is intolerable, the patient will be excluded from the study.

Preliminary results from the study that have been gathered to date indicate that the E508K HNF1A variant is indeed associated with greater response to Glipizide. Statistical analysis of the results is ongoing.

Example 3

Interventions for the Management of Diabetes

Creation of a Basic Mobile Individual Casual Game for Reinforcing Effective Eating Habits and Awareness The game would be developed for the Android platform using a touch-based interface. The instructional goal would be to reinforce the benefits of eating the right types of foods. A key intent would be to develop a gameplay style that is "addictive" to encourage long-term gameplay.

Potential Game Style: Forward-scroller (e.g., Minion Rush) or Side-scroller (e.g., Super Mario Bros), where collecting "good" food makes you stronger and "bad" food makes you weaker. Simple actions (e.g., jump with a slide up of your finger). Perhaps have a special "super food" that lets you power-up and counter the negative effect of a bad food. Reinforce concepts related to blood sugar via meters that go up and down over time or changes in the character's visible appearance. Reinforce the negative aspects of certain key bad foods via related monsters/etc. that are overcome as part of the game. To a limited degree, food options and bonuses offered in the gameplay can be chosen by the player based on selecting from available options (e.g., by selecting certain levels of the game to play—e.g., play a "high carb" level—or via selection of an "eating profile"). These options would be pre-determined to reflect typical and desired eating habits/foods in the target population. Players may choose based on what they like to eat or have eaten recently, or simply explore the impact of different preferences. These would not be "self-report" quality, but would be designed to educate/reinforce the pros and cons of different choices (e.g., choosing a high sugar/carb diet may allow them to go faster in the game but make few bonus options offered in the game and make it harder to make it all the way through the level).

Creation of a Virtual Longitudinal Interaction Game

This involves the creation of an electronic "friend" that the player takes care of and can come to identify with. The game would likely be developed for the personal computer to enable interrupts to the individual's normal activities (it is hard for one process to interrupt another on android, though it can send simple notifications). The instructional goal would be to reinforce the long-term effects of good or bad eating. An assessment goal would be to collect some self-report information on their eating habits and diabetes knowledge. A key intent would be to develop an interaction that the player would want to engage with in brief stints over a long period of time.

Potential Game Style: A virtual creature friend semi-randomly "pops up" on the player's device begging to be fed. From example, this friend could be an alien, weird monster, lego-type character, a virtual human, etc. (Not an animal since that would send mixed messages and have kids feeding their real pets human food that may be bad for them). The choice of avatar would be made from a set of pre-determined options. When the friend pops up, the player has to choose some foods to give it. In one design approach, we use this action as an opportunity to collect data on what the kids have been eating recently. In other words, the virtual friend is a copycat and always wants to eat what the child did. When fed well, it is "happy". In this mood, it may occasionally pop-up with a diabetes-related question (e.g., the friend asks "is this good for me to eat" or "how come I can't do xxx"?), or because it wants to play/get attention (e.g., to be petted). If fed badly (especially repeatedly over time), it gets sad (e.g., whimpers) and doesn't want to play (i.e., even if requested by the player—the player must now act to rectify the situation by feeding them well). We can reinforce awareness of certain negative behaviors in the actions of the friend. For instance, always wanting "more" of something sweet and encouraging the child to tell the friend no, it's bad for you.

Creation of a Casual Game with Real-Life Behavior Assessment

This involves involves creating a game with a supporting framework to enable capture and analysis of what a player is actually eating in real-life. Uses a "pay-to-play" concept where players must take pictures of their food and upload them in order to unlock capabilities/progress further in the game. To avoid issues with automated image analysis, we leverage crowd-sourcing via a service such as Amazon's Mechanical Turk. On a regular, frequent basis, the player needs to upload a picture they have taken with their device of their food (e.g., their breakfast). The crowd members assess the image against a set of diabetes-healthy-eating guidelines and provide a rating for the meal (Multiple crowd members can be used for each image to provide redundancy and improve the reliability of the measure). Once they have taken a picture, they play a casual game. At a later time—once the picture has been analyzed—they gain bonus capabilities in the game if they have been eating well (or perhaps encounter increased chances of difficulties if they have been eating poorly). Game uses a client-server architecture to keep track of player's data and behaviors.

Potential Game Style: The gameplay would be similar to the Option 2 game. The eating options and bonuses available in the game would be generated based on the pictures taken by the player.

System Elements: A number of back-end elements would be developed to support the data collection and assessment. The system would involve multiple game-server interactions, with the server providing data that influences the game, as well as collecting self-reports and other data generated by the game.

Creation of a Casual Game with Real-Life Behavior Assessment and Social Status

This encompasses the game approaches described above with the addition of graphical user interface (GUI) elements that enable players to improve the capabilities of their avatar in the game and basic social networking to provide a high-level means of interaction among players, such as via social sharing/localized leaderboard/shared rating capabilities. It does not provide a multi-player game capability, but may allow players to share avatars and eating profiles. Sharing between parents and kids via linked accounts will enable families to provide multiple data points on their eating habits and share awareness of diabetes issues.

Interaction Elements: We will explore multiple methods of sharing among players to encourage an excitement towards eating in a healthier manner. Methods may include: Rating systems for favorite meals, regional competitions for best eating habits (e.g., highest rated meal picture), pair-wise matching for enhanced collaborative learning and perhaps even rescue operations where players can swoop in to help a player figure out how to bring their unhappy/sick avatar back to full health. The level of effort includes multiple rounds of design and multiple development and deployment iterations to ensure the methods used have appeal and are effective at encouraging long-term participation. We will explore fun visual displays of progress, such as "you are what you eat" visualizations that use caricature to highlight poor eating habits.

System Elements: This effort would involve the creation of a rich set of interactions among players outside the game. For privacy and security reasons, chat capabilities are not anticipated. However, sharing of basic player "handles"/nicknames and rough geographical area are anticipated. No self-taken images will be posted without vetting by a moderator to ensure appropriateness and privacy.

Example 4

Genetic Score Calculation for the System DIABETESpredict

A theoretical model based on cases and controls to calculate a score for DIABETES predict, that includes 16 genetic markers, was constructed.

On the basis that the prevalence of type 2 diabetes mellitus (DM2) in Mexico (17%), 170 cases of DM2 and 830 controls were included in the model. On the basis of the frequency of the risk allele and odds ratio (OR) the expected frequency of risk alleles in cases (a) and in controls (c) was calculated, as well as the expected frequency of the non-risk allele cases (b) and in controls (d), for each of the markers included in the chip "DIABETESpredict." Considering that the markers are distributed in the population according to the Hardy-Weinberg law, the frequency of homozygous and heterozygous genotypes was calculated on the basis of the allele frequency and according to the following formula:

$$(a+b)^2 = a^2 + 2ab + b^2.$$

An algorithm was built that assigns risk genotypes to the number of cases and controls, selected at random, according to the previously calculated frequency for each genetic marker. This algorithm was constructed using the programs Access/Visual Basic. When a risk marker is positive in an individual (Case or Control) the OR for that marker is assigned if heterozygous and $OR^2$ if homozygous. When the genotype is negative for the risk allele a value of 1 is assigned. For each case and control the combined OR is calculated by multiplying the ORs for each of the 16 markers explored. Finally, the "fold change" is calculated (FC) by dividing the combined OR for each case and control by the median OR value of the controls group. With all the FCs a receiver operating characteristic (ROC) curve is generated, and the area under the curve (AUC) is calculated; the best sensitivity and specificity of the system is calculated.

Based on the data it was decided to set the cut point between positives and negatives at FC=1. Individuals with a FC≤1 have a risk that is equal to or less than median risk of the general population. Individuals with a FC>1 have a risk that is higher than the population median and we divide them into 3 groups:

Low risk: FC between 1.01 and 1.5
Intermediate risk: FC between 1.51 and 2.0
High risk: FC>2.0

The following values for sensitivity, specificity, positive predictive value (VPP) and negative predictive value (VPN) were determined for each tertile:

| FC | Sensitivity | Specificity | VPP | VPN |
|---|---|---|---|---|
| >1 | 71.8 | 51.3 | 23.2 | 89.9 |
| >1.5 | 35.9 | 82.3 | 29.3 | 86.2 |
| >2 | 25.3 | 92.5 | 41.0 | 85.8 |

TABLE 3

Values for OR, RAF, a, b, c and d for 16 SNPs

| Shows | SLC16A11 | INS-IGF2 | HNF1A | WFS1 | SLC30AB | PPARG | IGF2BP2 | CDKAL1 |
|---|---|---|---|---|---|---|---|---|
| OR | 1.29 | 1.28 | 5.48 | 1.13 | 1.12 | 1.1 | 1.12 | 1.05 |
| RAF | 0.3 | 0.92 | 0.02 | 0.76 | 0.75 | 0.91 | 0.25 | 0.34 |
| a | 177 | 468 | 50 | 391 | 385 | 459 | 135 | 177 |
| b | 323 | 32 | 450 | 109 | 115 | 41 | 365 | 323 |
| c | 150 | 460 | 10 | 380 | 375 | 455 | 125 | 170 |
| d | 350 | 40 | 490 | 120 | 125 | 45 | 375 | 330 |

| Shows | ADCY5 | JAZF1 | HHEX/IDE | KCNJ11 | KCNQ1 | TCF7L2 | FTO | CDKN2A/B |
|---|---|---|---|---|---|---|---|---|
| OR | 1.14 | 1.16 | 1.06 | 1.08 | 1.31 | 1.37 | 1.17 | 1.08 |
| RAF | 0.73 | 0.67 | 0.64 | 0.39 | 0.73 | 0.23 | 0.27 | 0.89 |
| a | 377 | 351 | 327 | 204 | 390 | 145 | 150 | 449 |
| b | 123 | 149 | 173 | 296 | 110 | 355 | 350 | 51 |
| c | 365 | 335 | 320 | 195 | 365 | 115 | 135 | 445 |
| d | 135 | 165 | 180 | 305 | 135 | 385 | 365 | 55 |

Equivalents

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, including patent documents, disclosed herein are incorporated by reference in their entirety, particularly for the disclosure referenced herein.

REFERENCES

1. Shaw et al, 2010. Global estimates of the prevalence of diabetes for 2010 and 2030. Diabetes Research and Clinical Practice: 293-301.
2. International Diabetes Federation, 2013.
3. Morris et al., Large-scale association analysis provides insights into the genetic architecture and pathophysiology of type 2 diabetes. (2012) Nature Genetics, Vol. 44(9): 981-990.
4. Voight et al., Twelve type 2 diabetes susceptibility loci identified through large-scale association analysis. (2010) Nature Genetics, Vol. 42(7): 579-589.
5. Diabetes Genetics Replication and Meta-analysis (DIAGRAM) Consortium, Genome-wide trans-ancestry meta-analysis provides insight into the genetic architecture of type 2 diabetes susceptibility. (2014) Nature Genetics, Vol. 46(3): 234-244.
6. Albrechtsen et al., Exome sequencing-driven discovery of coding polymorphisms associated with common metabolic phenotypes. (2013) Diabetologica, Vol. 56(2): 298-310.
7. Lohmueller et al., Whole-exome sequencing of 2000 Danish individuals and the role of rare coding variants in type 2 diabetes. (2013) American Journal of Human Genetics, Vol. 93(6): 1072-1086.
8. Steinthorsdottir et al., Identification of low-frequency and rare sequence variants with elevated or reduced risk of type 2 diabetes. (2014) Nature Genetics, Vol. 46(3): 294-298.
9. Villalpando et al., Prevalence and distribution of type 2 diabetes mellitus in Mexican adult population: a probabilistic survey. (2010) Salud Pública de México, Vol 52: S19-S26.
10. US Department of Health and Human Services, Centers for Disease Control and Prevention, 2011.
11. The SIGMA Type 2 Diabetes Consortium, Sequence Variants in SLC16A11 are a Common Risk Factor for Type 2 Diabetes in Mexico. Nature, Vol. 506 (7486): 97-101 (2013).
12. Patterson et al., Population Structure and Eigenanalysis. PLoS Genetics, Vol. 2(12): e190 (2006).
13. Ibid.
14. The 1000 Genomes Project Consortium, An Integrated Map of Genetic Variation from 1,092 Human Genomes. Nature, Vol. 491(7422): 56-65 (2012).
15. Williams et al., Phasing of Many Thousands of Genotyped Samples. American Journal of Human Genetics, Vol. 91(2): 238-251 (2012).
16. Howie et al., A Flexible and Accurate Genotype Imputation Method for the Next Generation of Genome-Wide Association Studies. PLoS Genetics, Vol. 5(6): e1000529 (2009).
17. Zaitlen, et al. Informed Conditioning on Clinical Covariates Increases Power in Case-Control Association Studies. PLoS Genetics, Vol. 8(11): e1003032 (2012).
18. Villalpando et al., Prevalence and Distribution of Type 2 Diabetes Mellitus in the Mexican Adult Population: A Probabilistic Survey. Salud Pública de México 52, S19-S26 (2010).
19. Purcell et al., PLINK: A Tool Set for Whole-Genome Association and Population-Based Linkage Analyses. The American Journal of Human Genetics, Vol. 81: 559-575 (2007).
20. Devlin et al., Genomic Control for Association Studies. Biometrics Vol. 55(4): 997-1004 (1999).
21. Alexander et al., Fast model-based estimation of ancestry in unrelated individuals. Genome research, Vol. 19(9): 1655-1664 (2009).
22. Li et al., Worldwide Human Relationships Inferred from Genome-Wide Patterns of Variation. Science, Vol. 319(5866): 1100-1104 (2008).
23. Baran et al., Fast and Accurate Inference of Local Ancestry in Latino Populations. Bioinformatics, Vol. 28(10): 1359-1367 (2012).

24. Li 2008; Reich et al., Reconstructing Native American Population History. Nature, Vol. 488(7411): 370-374 (2012).
25. Ibid.
26. Behar et al., The Genome-Wide Structure of the Jewish People. Nature, Vol. 466(7303): 238-242 (2010).
27. The International HapMap 3 Consortium, Integrating Common and Rare Genetic Variation in Diverse Human Populations. Nature, Vol. 467(7311): 52-58 (2010), Supplemental Information.
28. Delaneau et al., A Linear Complexity Phasing Method for Thousands of Genomes. Nature Methods, Vol. 9: 179-181, (2012).
29. Willer et al. METAL: Fast and Efficient Meta-Analysis of Genomewide Association Scans. Bioinformatics, Vol. 26: 2190-2191 (2010).
30. Prium et al. LocusZoom: Regional Visualization of Genome-Wide Association Scan Results. Bioinformatics, Vol. 26: 2336-2337 (2010).

The invention claimed is:

1. A genotyping tool configured to genotype a nucleic acid-containing sample obtained from a human subject to provide genotype data, said tool comprising an array having a plurality of oligonucleotide probe pairs, each of said probe pairs comprising a first allele-specific probe for a first allele of a single nucleotide polymorphism (SNP) and a second allele-specific probe for a second allele of the SNP, wherein each first and second allele-specific probe is covalently attached to a fluorophore, a quencher and/or a minor groove binding domain, wherein said plurality of oligonucleotide probe pairs comprises probe pairs configured to interrogate all of the following single nucleotide polymorphisms:

rs75493593 in SLC16A11;
rs483353044 in HNF1A;
rs7903146 in TCF7L2;
rs10811661 in CDKN2A/B;
rs7756992 in CDKAL1;
rs3802177 in SLC30A8;
rs4402960 in IGF2BP2;
rs9936385 in FTO;
rs1801282 in PPARG;
rs1111875 in HHEX/IDE;
rs11717195 in ADCY5;
rs849135 in JAZF1;
rs4458523 WSF1;
rs149483638 in IGF2;
rs2237897 KCNQ1; and
rs5219 in KCNJ11, and wherein the total number of different SNPs for which oligonucleotide probe pairs are present in said genotyping tool does not exceed twenty SNPs.

2. The genotyping tool of claim 1, wherein the nucleotide sequence of each of the first and second allele-specific probes is 13 to 18 nucleotides in length and is, or is complementary to, a contiguous SNP context sequence spanning the polymorphic site which context sequence is selected from the group consisting of SEQ ID NO: 1-16.

3. The genotyping tool of claim 1, wherein the array further comprises a primer pair for each of said single nucleotide polymorphisms, said primer pair for each single nucleotide polymorphism comprising an oligonucleotide primer that hybridizes to a target sequence, upstream of the SNP and an oligonucleotide primer that hybridizes to a target sequence downstream of the SNP.

4. The genotyping tool of claim 1, wherein the genotyping tool further comprise one or more reagents for amplification of DNA comprising said single nucleotide polymorphisms and/or for detection of said allele specific probes.

5. The genotyping tool of claim 4, wherein the one or more reagents comprises Taq DNA polymerase.

6. A genotyping tool configured to genotype a nucleic acid-containing sample obtained from a human subject to provide genotype data, said tool comprising an array having a plurality of oligonucleotide probe pairs, each of said probe pairs comprising a first allele-specific probe for a first allele of a single nucleotide polymorphism (SNP) and a second allele-specific probe for a second allele of the SNP, wherein each first and second allele-specific probe is covalently attached to a surface, wherein said plurality of oligonucleotide probe pairs comprises probe pairs configured to interrogate all of the following single nucleotide polymorphisms:

rs75493593 in SLC16A11;
rs483353044 in HNF1A;
rs7903146 in TCF7L2;
rs10811661 in CDKN2A/B;
rs7756992 in CDKAL1;
rs3802177 in SLC30A8;
rs4402960 in IGF2BP2;
rs9936385 in FTO;
rs1801282 in PPARG;
rs1111875 in HHEX/IDE;
rs11717195 in ADCY5;
rs849135 in JAZF1;
rs4458523 WSF1;
rs149483638 in IGF2;
rs2237897 KCNQ1; and
rs5219 in KCNJ11, and wherein the total number of different SNPs for which oligonucleotide probe pairs are present in said genotyping tool does not exceed twenty SNPs.

7. The genotyping tool of claim 6, wherein the nucleotide sequence of each of the first and second allele-specific probes is 13 to 18 nucleotides in length and is, or is complementary to, a contiguous SNP context sequence spanning the polymorphic site which context sequence is selected from the group consisting of SEQ ID NO: 1-16.

8. The genotyping tool of claim 6, wherein the array further comprises a primer pair for each of said single nucleotide polymorphisms, said primer pair for each single nucleotide polymorphism comprising an oligonucleotide primer that hybridizes to a target sequence upstream of the SNP and an oligonucleotide primer that hybridizes to a target sequence downstream of the SNP.

9. The genotyping tool of claim 6, wherein the genotyping tool further comprise one or more reagents for amplification of DNA comprising said single nucleotide polymorphisms and/or for detection of said allele specific probes.

10. The genotyping tool of claim 9, wherein the one or more reagents comprises Taq DNA polymerase.

* * * * *

SEQUENCE LISTING

<160> NUMBER OF SEQ ID NOS: 16

<210> SEQ ID NO 1
<211> LENGTH: 51
<212> TYPE: DNA
<213> ORGANISM: Homo sapiens

<400> SEQUENCE: 1
tagagagcta agcactttt agataytata taatttaatt gccgtatgag g        51

<210> SEQ ID NO 2
<211> LENGTH: 51
<212> TYPE: DNA
<213> ORGANISM: Homo sapiens

<400> SEQUENCE: 2
cagctcacct ccagctttag ttttcycatg acagtaagtc tattaccctc c        51

<210> SEQ ID NO 3
<211> LENGTH: 51
<212> TYPE: DNA
<213> ORGANISM: Homo sapiens

<400> SEQUENCE: 3
atattccccc ctgtatttta gttttrgatc tacagttatg tagcaatgag c        51

<210> SEQ ID NO 4
<211> LENGTH: 51
<212> TYPE: DNA
<213> ORGANISM: Homo sapiens

<400> SEQUENCE: 4
taaggaacca aaggaagaaa ttcatrtcat ggtgcaatgc acattttatc t        51

<210> SEQ ID NO 5
<211> LENGTH: 51
<212> TYPE: DNA
<213> ORGANISM: Homo sapiens

<400> SEQUENCE: 5
agtaaggtag gatggacagt agattkaaga tactgattgt gtttgcaaac a        51

<210> SEQ ID NO 6
<211> LENGTH: 51
<212> TYPE: DNA
<213> ORGANISM: Homo sapiens

<400> SEQUENCE: 6
catatgaaga gggattttt tgcctycttg gttcactgca tattcccagt a        51

<210> SEQ ID NO 7
<211> LENGTH: 51

```
<212> TYPE: DNA
<213> ORGANISM: Homo sapiens

<400> SEQUENCE: 7
gaccctgagt gcaggttcag acgtcyagag gaaatgactt gatggtacgg a            51

<210> SEQ ID NO 8
<211> LENGTH: 51
<212> TYPE: DNA
<213> ORGANISM: Homo sapiens

<400> SEQUENCE: 8
ttgaacaggg ctttatgtcc gaggaygatt ataaaattta acaattagga g            51

<210> SEQ ID NO 9
<211> LENGTH: 51
<212> TYPE: DNA
<213> ORGANISM: Homo sapiens

<400> SEQUENCE: 9
accactgctc tataagcaag agtacrtcac caagaaattt aaattcagat c            51

<210> SEQ ID NO 10
<211> LENGTH: 51
<212> TYPE: DNA
<213> ORGANISM: Homo sapiens

<400> SEQUENCE: 10
tcagtggtgc ccagggagct ggggaygagg ggcctcatcc ttcccctgag c            51

<210> SEQ ID NO 11
<211> LENGTH: 51
<212> TYPE: DNA
<213> ORGANISM: Homo sapiens

<400> SEQUENCE: 11
cgctggcggg cacggtacct gggctyggca gggtcctctg ccaggcgtgt c            51

<210> SEQ ID NO 12
<211> LENGTH: 51
<212> TYPE: DNA
<213> ORGANISM: Homo sapiens

<400> SEQUENCE: 12
gccagccctc tacagccaca agcccraggt ggcccagtac acccacacgg g            51

<210> SEQ ID NO 13
<211> LENGTH: 51
<212> TYPE: DNA
<213> ORGANISM: Homo sapiens

<400> SEQUENCE: 13
aatttctttc ctgacctcac agccakattg tactttaaag ttcctcccac a            51

<210> SEQ ID NO 14
<211> LENGTH: 51
<212> TYPE: DNA
<213> ORGANISM: Homo sapiens

<400> SEQUENCE: 14
ggaagcagct cccccgtctc tggggkaggc gtggctggag gggaggctgg a            51

<210> SEQ ID NO 15
```

```
<211> LENGTH: 51
<212> TYPE: DNA
<213> ORGANISM: Homo sapiens

<400> SEQUENCE: 15
tttgggggtc tggggaaacc atctcytgga gagtttgaac gatgtaagaa a         51

<210> SEQ ID NO 16
<211> LENGTH: 51
<212> TYPE: DNA
<213> ORGANISM: Homo sapiens

<400> SEQUENCE: 16
aactctggga gattctccta ttgacscaga aagcgattcc ttcactgata c         51
```